(12) United States Patent
Hilpert et al.

(10) Patent No.: US 9,273,042 B2
(45) Date of Patent: Mar. 1, 2016

(54) 5-AMINO[1,4]THIAZINES AS BACE 1 INHIBITORS

(71) Applicant: Hoffmann-La Roche Inc., Nutley, NJ (US)

(72) Inventors: Hans Hilpert, Muenchenstein (CH); Thomas Woltering, Freiburg (DE)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/400,448

(22) PCT Filed: May 21, 2013

(86) PCT No.: PCT/EP2013/060352
§ 371 (c)(1),
(2) Date: Nov. 11, 2014

(87) PCT Pub. No.: WO2013/174781
PCT Pub. Date: Nov. 28, 2013

(65) Prior Publication Data
US 2015/0141413 A1    May 21, 2015

(30) Foreign Application Priority Data
May 24, 2012   (EP) .................................. 12169353

(51) Int. Cl.
*C07D 417/12*   (2006.01)
(52) U.S. Cl.
CPC ................................... *C07D 417/12* (2013.01)
(58) Field of Classification Search
None
See application file for complete search history.

(56) References Cited

FOREIGN PATENT DOCUMENTS

| WO | 2011020806 | | 2/2011 |
|---|---|---|---|
| WO | WO 2012139425 A1 | * | 10/2012 |
| WO | WO 2013028670 A1 | * | 2/2013 |

OTHER PUBLICATIONS

The English translation of the Colombian Office Action, issued on Nov. 14, 2015, in the related Colombian Patent Application No. 14-249385.

* cited by examiner

*Primary Examiner* — Heidi Reese

(57) ABSTRACT

The present invention provides a compound of formula I having BACE1 inhibitory activity, their manufacture, pharmaceutical compositions containing them and their use as therapeutically active substances. The active compounds of the present invention are useful in the therapeutic and/or prophylactic treatment of e.g. Alzheimer's disease.

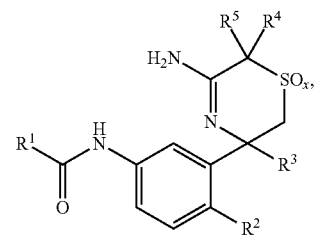

14 Claims, No Drawings

5-AMINO[1,4]THIAZINES AS BACE 1 INHIBITORS

CROSS-REFERENCE TO RELATED APPLICATIONS

This application is a National Stage Application of PCT/EP2013/060352 filed May 21, 2013, which claims priority from European Patent Application 12169353.5, filed on May 24, 2012. The priority of both said PCT and European Patent Application are claimed. Each of prior mentioned applications is hereby incorporated by reference herein in its entirety.

BACKGROUND ART

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science.* 2002 Jul. 19; 297(5580):353-6, Selkoe, Cell biology of the amyloid beta-protein precursor and the mechanism of Alzheimer's disease, *Annu Rev Cell Biol.* 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science.* 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat. Neurosci.* 2001 March; 4(3):231-2, Roberds et al., BACE knockout mice are healthy despite lacking the primary beta-secretase activity in brain: implications for Alzheimer's disease therapeutics, *Hum Mol Genet.* 2001 Jun. 1; 10(12):1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol. Chem.* 2007 Sep. 7; 282(36):26326). It is thus presumed that inhibitors of BACE1 activity can be useful agents for therapeutic intervention in Alzheimer's disease (AD).

Furthermore, the formation, or formation and deposition, of β-amyloid peptides in, on or around neurological tissue (e.g., the brain) are inhibited by the present compounds, i.e. inhibition of the Aβ-production from APP or an APP fragment.

WO2012139425 describes iminothiazine compounds and mono- and dioxides as BACE1 inhibitors. WO2011020806 describes 3-Amino-5-phenyl-5,6-dihydro-2H-[1,4]oxazines as BACE1 inhibitors. WO2011069934 describes 2-Amino-5,5-difluoro-5,6-dihydro-4H-[1,3]oxazin-4-yl)-phenyl]-amide as BACE1 inhibitors. WO2011029803 describes the use of aminodihydrothiazine derivatives for the treatment or prevention of metabolic diseases such as preferably diabetes, particularly type 2 diabetes. The compounds are BACE2 inhibitors.

The present invention provides novel compounds of formula I, their manufacture, medicaments based on a compound in accordance with the invention and their production as well as the use of compounds of formula I in the control or prevention of illnesses such as Alzheimer's disease. The novel compounds of formula I have improved pharmacological properties.

FIELD OF THE INVENTION

The present invention provides 5-amino-[1,4]thiazines having BACE1 inhibitory properties, their manufacture, pharmaceutical compositions containing them and their use as therapeutically active substances.

SUMMARY OF THE INVENTION

The present invention provides a compound of formula I,

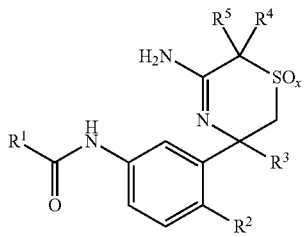

wherein the substituents and variables are as described below and in the claims, or a pharmaceutically acceptable salt thereof.

The present compounds have Asp2 (β-secretase, BACE1 or Memapsin-2) inhibitory activity and may therefore be used in the therapeutic and/or prophylactic treatment of diseases and disorders characterized by elevated β-amyloid levels and/or β-amyloid oligomers and/or β-amyloid plaques and further deposits, particularly Alzheimer's disease.

DETAILED DESCRIPTION OF THE INVENTION

The present invention provides a compound of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with inhibition of BACE1, such as Alzheimer's disease. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. Particular "$C_{1-6}$-alkyl" are "$C_{1-3}$-alkyl". Specific groups are methyl and ethyl. Most specific is methyl.

The term "halogen-$C_{1-6}$-alkyl", alone or in combination with other groups, refers to $C_{1-6}$-alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-6}$-alkyl and a particular "halogen-$C_{1-3}$-alkyl" is fluoro-$C_{1-3}$-alkyl. Examples are trifluoromethyl, difluoromethyl, fluoromethyl and the like. A specific group is difluoromethyl.

The term "cyano-$C_{1-6}$-alkyl", alone or in combination with other groups, refers to $C_{1-6}$-alkyl as defined herein, which is substituted by one or multiple cyano, particularly 1 cyano. Examples are cyanomethyl, cyanoethyl and the like.

The term "$C_{1-6}$-alkoxy-$C_{1-6}$-alkyl", alone or in combination with other groups, refers to $C_{1-6}$-alkyl as defined herein, which is substituted by one or multiple $C_{1-6}$-alkoxy, as defined herein, particularly 1 $C_{1-6}$-alkoxy. Particular "$C_{1-6}$-alkoxy-$C_{1-6}$-alkyl" is methoxy-$C_{1-6}$-alkyl. Examples are methoxymethyl, methoxyethyl and the like.

The term "cyano", alone or in combination with other groups, refers to N≡C—(NC—).

The term "halogen", alone or in combination with other groups, denotes chloro (Cl), iodo (I), fluoro (F) and bromo (Br). Particular "halogen" is Cl and F. A specific group is F.

The term "heteroaryl", alone or in combination with other groups, refers to an aromatic carbocyclic group of having a single 4 to 8 membered ring or multiple condensed rings comprising 6 to 14, in particular 6 to 10 ring atoms and containing 1, 2 or 3 heteroatoms individually selected from N, O and S, in particular 1N or 2N, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular "heteroaryl" are pyridinyl and pyrazinyl. Specific "heteroaryl" are pyridin-2-yl and pyrazin-2-yl.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt, propoxy, isopropoxy (i-propoxy), n-butoxy, i-butoxy (isobutoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. Specific is methoxy.

The term "halogen-$C_{1-6}$-alkoxy", alone or in combination with other groups, refers to $C_{1-6}$-alkoxy as defined herein, which is substituted by one or multiple halogens, in particular fluoro. Particular "halogen-$C_{1-6}$-alkoxy" are fluoro-$C_{1-6}$-alkoxy. Specific "halogen-$C_{1-6}$-alkoxy" is difluoromethoxy.

The term "$C_{2-6}$-alkynyl-$C_{1-6}$-alkoxy", alone or in combination with other groups, refers to $C_{1-6}$-alkoxy as defined herein, which is substituted by one or multiple $C_{2-6}$-alkynyl as defined herein, in particular 1 $C_{2-6}$-alkynyl.

The term "$C_{2-6}$-alkynyl", alone or in combination with other groups, denotes a monovalent linear or branched saturated hydrocarbon group of 2 to 6 carbon atoms, in particular from 2 to 4 carbon atoms, and comprising one, two or three triple bonds. Examples of $C_{2-6}$-alkynyl include ethynyl, propynyl, prop-2-ynyl, isopropynyl and n-butynyl.

The term "aryl" denotes a monovalent aromatic carbocyclic mono- or bicyclic ring system comprising 6 to 10 carbon ring atoms. Examples of aryl moieties include phenyl and naphthyl. Specific "aryl" is phenyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Particular acids are formic acid, trifluoroacetic acid and hydrochloric acid. Specific acids are hydrochloric acid, trifluoroacetic acid and fumaric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" (IC50) denotes the concentration of a particular compound required for obtaining 50% inhibition of a biological process in vitro. IC50 values can be converted logarithmically to pIC50 values (−log IC50), in which higher values indicate exponentially greater potency. The IC50 value is not an absolute value but depends on experimental conditions e.g. concentrations employed. The IC50 value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. The term "amino-protecting group" (here also $P^1$) denotes groups intended to protect an amino group and includes benzyl, benzyloxycarbonyl (carbobenzyloxy, CBZ), 9-Fluorenylmethyloxycarbonyl (FMOC), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", $4^{th}$ ed, John Wiley & Sons, Inc., New York, N.Y., 2007, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups. Particular amino-protecting groups are tert-butoxycarbonyl group and dimethoxytrityl.

The term "leaving group" denotes the group with the meaning conventionally associated with it in synthetic organic chemistry, i.e., an atom or group displaceable under substitution reaction conditions. Examples of leaving groups include halogen, in particular bromo, alkane- or arylenesulfonyloxy, such as methanesulfonyloxy, ethanesulfonyloxy, thiomethyl, benzenesulfonyloxy, tosyloxy, dihalophosphinoyloxy, optionally substituted benzyloxy, isopropyloxy, and acyloxy.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being nontoxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

One embodiment of the invention provides a compound of formula I,

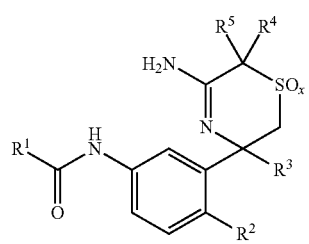

wherein
R$^1$ is selected from the group consisting of
  i) aryl,
  ii) aryl substituted by 1-4 substituents individually selected from cyano, cyano-C$_{1-6}$-alkyl, halogen, halogen-C$_{1-6}$-alkoxy, halogen-C$_{1-6}$-alkyl, C$_{1-6}$-alkoxy, C$_{1-6}$-alkoxy-C$_{1-6}$-alkyl, C$_{2-6}$-alkynyl-C$_{1-6}$-alkoxy, C$_{2-6}$-alkynyl and C$_{1-6}$-alkyl,
  iii) heteroaryl, and
  iv) heteroaryl substituted by 1-4 substituents individually selected from cyano, cyano-C$_{1-6}$-alkyl, halogen, halogen-C$_{1-6}$-alkoxy, halogen-C$_{1-6}$-alkyl, C$_{1-6}$-alkoxy, C$_{1-6}$-alkoxy-C$_{1-6}$-alkyl, C$_{2-6}$-alkynyl-C$_{1-6}$-alkoxy, C$_{2-6}$-alkynyl and C$_{1-6}$-alkyl;
R$^2$ is selected from the group consisting of
  i) hydrogen,
  ii) C$_{1-6}$-alkyl, and
  iii) halogen;
R$^3$ is selected from the group consisting of
  i) C$_{1-6}$-alkyl, and
  ii) halogen-C$_{1-6}$-alkyl,
R$^4$ is selected from the group consisting of
  i) C$_{1-6}$-alkyl,
  ii) halogen-C$_{1-6}$-alkyl, and
  iii) hydrogen,
R$^5$ is selected from the group consisting of
  i) C$_{1-6}$-alkyl,
  ii) halogen-C$_{1-6}$-alkyl, and
  iii) hydrogen,
or R$^4$ and R$^5$ together form a C$_{3-7}$-cycloalkyl ring, optionally substituted by one or more halogen, x is 0 or 2,
or pharmaceutically acceptable salts thereof.

One embodiment of the invention provides a compound of formula I which is a compound of formula Ia,

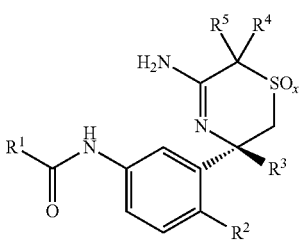

wherein
R$^1$ is selected from the group consisting of
  i) aryl,
  ii) aryl substituted by 1-4 substituents individually selected from cyano, cyano-C$_{1-6}$-alkyl, halogen, halogen-C$_{1-6}$-alkoxy, halogen-C$_{1-6}$-alkyl, C$_{1-6}$-alkoxy, C$_{1-6}$-alkoxy-C$_{1-6}$-alkyl, C$_{2-6}$-alkynyl-C$_{1-6}$-alkoxy, C$_{2-6}$-alkynyl and C$_{1-6}$-alkyl,
  iii) heteroaryl, and
  iv) heteroaryl substituted by 1-4 substituents individually selected from cyano, cyano-C$_{1-6}$-alkyl, halogen, halogen-C$_{1-6}$-alkoxy, halogen-C$_{1-6}$-alkyl, C$_{1-6}$-alkoxy, C$_{1-6}$-alkoxy-C$_{1-6}$-alkyl, C$_{2-6}$-alkynyl-C$_{1-6}$-alkoxy, C$_{2-6}$-alkynyl and C$_{1-6}$-alkyl;
R$^2$ is selected from the group consisting of
  i) hydrogen,
  ii) C$_{1-6}$-alkyl, and
  iii) halogen;
R$^3$ is selected from the group consisting of
  i) C$_{1-6}$-alkyl, and
  ii) halogen-C$_{1-6}$-alkyl,
R$^4$ is selected from the group consisting of
  i) C$_{1-6}$-alkyl,
  ii) halogen-C$_{1-6}$-alkyl, and
  iii) hydrogen,
R$^5$ is selected from the group consisting of
  i) C$_{1-6}$-alkyl,
  ii) halogen-C$_{1-6}$-alkyl, and
  iii) hydrogen,
or R$^4$ and R$^5$ together form a C$_{3-7}$-cycloalkyl ring, optionally substituted by one or more halogen, x is 0 or 2,
or pharmaceutically acceptable salts thereof.

One embodiment of the invention provides a compound of formula Ia,

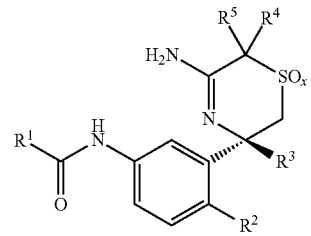

wherein
R$^1$ is selected from the group consisting of
  i) pyridinyl substituted by one substituent selected from cyano, halogen and halogen-C$_{1-6}$-alkoxy, and
  ii) pyrazinyl substituted by one substituent selected from C$_{1-6}$-alkoxy and halogen-C$_{1-6}$-alkyl;
R$^2$ is halogen,
R$^3$ is C$_{1-6}$-alkyl,
R$^4$ is selected from the group consisting of
  i) C$_{1-6}$-alkyl, and
  ii) hydrogen,
R$^5$ is selected from the group consisting of
  i) C$_{1-6}$-alkyl, and
  ii) hydrogen,
or R$^4$ and R$^5$ together form a C$_{3-7}$-cycloalkyl ring,
x is 2,
or pharmaceutically acceptable salts thereof.

A certain embodiment of the invention provides a compound of formula I as described herein, wherein R$^2$ is halogen.

A certain embodiment of the invention provides a compound of formula I as described herein, wherein R$^2$ is F.

A certain embodiment of the invention provides a compound of formula I as described herein, wherein R$^3$ is C$_{1-6}$-alkyl.

A certain embodiment of the invention provides a compound of formula I as described herein, wherein R$^3$ is methyl.

A certain embodiment of the invention provides a compound of formula I as described herein, wherein R$^4$ is C$_{1-6}$-alkyl.

A certain embodiment of the invention provides a compound of formula I as described herein, wherein R$^4$ is methyl.

A certain embodiment of the invention provides a compound of formula I as described herein, wherein R$^4$ is hydrogen.

A certain embodiment of the invention provides a compound of formula I as described herein, wherein R$^5$ is halogen-C$_{1-6}$-alkyl.

A certain embodiment of the invention provides a compound of formula I as described herein, wherein $R^5$ is $C_{1-6}$-alkyl.

A certain embodiment of the invention provides a compound of formula I as described herein, wherein $R^5$ is methyl.

A certain embodiment of the invention provides a compound of formula I as described herein, wherein $R^5$ is hydrogen.

A certain embodiment of the invention provides a compound of formula I as described herein, wherein $R^5$ is halogen-$C_{1-6}$-alkyl.

A certain embodiment of the invention provides a compound of formula I as described herein, wherein $R^4$ and $R^5$ are hydrogen.

A certain embodiment of the invention provides a compound of formula I as described herein, wherein $R^4$ and $R^5$ are $C_{1-6}$-alkyl.

A certain embodiment of the invention provides a compound of formula I as described herein, wherein $R^4$ and $R^5$ are methyl.

A certain embodiment of the invention provides a compound of formula I as described herein, wherein $R^4$ and $R^5$ together form a $C_{3-7}$-cycloalkyl ring.

A certain embodiment of the invention provides a compound of formula I as described herein, wherein $R^4$ and $R^5$ together form a $C_{3-7}$-cycloalkyl ring substituted by one or more halogen.

A certain embodiment of the invention provides a compound of formula I as described herein, wherein $R^4$ and $R^5$ together form a $C_{3-7}$-cycloalkyl ring substituted by one halogen.

A certain embodiment of the invention provides a compound of formula I as described herein, wherein $R^4$ and $R^5$ together form a cyclobutyl or cyclopentyl ring.

A certain embodiment of the invention provides a compound of formula I as described herein, wherein $R^4$ and $R^5$ together form a cyclobutyl ring.

A certain embodiment of the invention provides a compound of formula I as described herein, wherein $R^4$ and $R^5$ together form a cyclopentyl ring.

A certain embodiment of the invention provides a compound of formula I as described herein, wherein $R^1$ is heteroaryl substituted by one substituent individually selected from cyano, halogen, halogen-$C_{1-6}$-alkyl, halogen-$C_{1-6}$-alkoxy and $C_{1-6}$-alkoxy.

A certain embodiment of the invention provides a compound of formula I as described herein, wherein $R^1$ is pyridinyl or pyrazinyl, each substituted by one substituent individually selected from cyano, halogen, halogen-$C_{1-6}$-alkyl, halogen-$C_{1-6}$-alkoxy and $C_{1-6}$-alkoxy.

A certain embodiment of the invention provides a compound of formula I as described herein, wherein $R^1$ is cyano-pyridinyl, chloro-pyridinyl, difluoromethoxy-pyridinyl, methoxy-pyrazinyl or difluoromethyl-pyrazinl.

A certain embodiment of the invention provides a compound of formula I as described herein, wherein $R^1$ is 5-cyano-pyridin-2-yl, 5-chloro-pyridin-2-yl, 5-difluoromethoxy-pyridin-2-yl, 5-methoxy-pyrazin-2-yl or 5-difluoromethyl-pyrazin-2-yl.

A certain embodiment of the invention provides a compound of formula I as described herein, wherein x is 2.

A certain embodiment of the invention provides a compound of formula I as described herein, wherein x is 0.

A certain embodiment of the invention provides a compound of formula I as described herein, selected from the group consisting of 5-Cyano-pyridine-2-carboxylic acid [3-((R)-5-amino-3-methyl-3,6-dihydro-2H-[1,4]thiazin-3-yl)-4-fluoro-phenyl]-amide, 5-Difluoromethoxy-pyridine-2-carboxylic acid [3-((R)-5-amino-3-methyl-1,1-dioxo-1,2,3,6-tetrahydro-1$\lambda^6$-[1,4]thiazin-3-yl)-4-fluoro-phenyl]-amide, 5-Chloro-pyridine-2-carboxylic acid [3-((R)-5-amino-3,6,6-trimethyl-1,1-dioxo-1,2,3,6-tetrahydro-1$\lambda^6$-[1,4]thiazin-3-yl)-4-fluoro-phenyl]-amide, 5-Cyano-pyridine-2-carboxylic acid [3-((R)-5-amino-3,6,6-trimethyl-1,1-dioxo-1,2,3,6-tetrahydro-1$\lambda^6$-[1,4]thiazin-3-yl)-4-fluoro-phenyl]-amide, 5-Methoxy-pyrazine-2-carboxylic acid [3-((R)-5-amino-3,6,6-trimethyl-1,1-dioxo-1,2,3,6-tetrahydro-1$\lambda^6$-[1,4]thiazin-3-yl)-4-fluoro-phenyl]-amide, 5-Difluoromethyl-pyrazine-2-carboxylic acid [3-((R)-5-amino-3,6,6-trimethyl-1,1-dioxo-1,2,3,6-tetrahydro-1$\lambda^6$-[1,4]thiazin-3-yl)-4-fluoro-phenyl]-amide, 5-Cyano-pyridine-2-carboxylic acid [3-((R)-5-amino-3-methyl-1,1-dioxo-1,2,3,6-tetrahydro-1$\lambda^6$-[1,4]thiazin-3-yl)-4-fluoro-phenyl]-amide, 5-Chloro-pyridine-2-carboxylic acid [3-((R)-5-amino-3-methyl-1,1-dioxo-1,2,3,6-tetrahydro-1$\lambda^6$-[1,4]thiazin-3-yl)-4-fluoro-phenyl]-amide, 5-Cyano-pyridine-2-carboxylic acid [3-((R)-9-amino-7-methyl-5,5-dioxo-5$\lambda^6$-thia-8-aza-spiro[3.5]non-8-en-7-yl)-4-fluoro-phenyl]-amide, 5-Chloro-pyridine-2-carboxylic acid [3-((R)-9-amino-7-methyl-5,5-dioxo-5$\lambda^6$-thia-8-aza-spiro[3.5]non-8-en-7-yl)-4-fluoro-phenyl]-amide, and 5-Cyano-pyridine-2-carboxylic acid [3-((R)-10-amino-8-methyl-6,6-dioxo-6$\lambda^6$-thia-9-aza-spiro[4.5]dec-9-en-8-yl)-4-fluoro-phenyl]-amide, or a pharmaceutical acceptable salt thereof.

A certain embodiment of the invention provides a compound of formula I as described herein which is 5-Cyano-pyridine-2-carboxylic acid [3-((R)-5-amino-3-methyl-3,6-dihydro-2H-[1,4]thiazin-3-yl)-4-fluoro-phenyl]-amide.

A certain embodiment of the invention provides a compound of formula I as described herein which is 5-Difluoromethoxy-pyridine-2-carboxylic acid [3-((R)-5-amino-3-methyl-1,1-dioxo-1,2,3,6-tetrahydro-1$\lambda^6$-[1,4]thiazin-3-yl)-4-fluoro-phenyl]-amide.

A certain embodiment of the invention provides a compound of formula I as described herein which is 5-Chloro-pyridine-2-carboxylic acid [3-((R)-5-amino-3,6,6-trimethyl-1,1-dioxo-1,2,3,6-tetrahydro-1$\lambda^6$-[1,4]thiazin-3-yl)-4-fluoro-phenyl]-amide.

A certain embodiment of the invention provides a compound of formula I as described herein which is 5-Cyano-pyridine-2-carboxylic acid [3-((R)-5-amino-3,6,6-trimethyl-1,1-dioxo-1,2,3,6-tetrahydro-1$\lambda^6$-[1,4]thiazin-3-yl)-4-fluoro-phenyl]-amide.

A certain embodiment of the invention provides a compound of formula I as described herein which is 5-Methoxy-pyrazine-2-carboxylic acid [3-((R)-5-amino-3,6,6-trimethyl-1,1-dioxo-1,2,3,6-tetrahydro-1$\lambda^6$-[1,4]thiazin-3-yl)-4-fluoro-phenyl]-amide.

A certain embodiment of the invention provides a compound of formula I as described herein which is 5-Difluoromethyl-pyrazine-2-carboxylic acid [3-((R)-5-amino-3,6,6-trimethyl-1,1-dioxo-1,2,3,6-tetrahydro-1$\lambda^6$-[1,4]thiazin-3-yl)-4-fluoro-phenyl]-amide.

A certain embodiment of the invention provides a compound of formula I as described herein which is 5-Cyanopyridine-2-carboxylic acid [3-((R)-5-amino-3-methyl-1,1-dioxo-1,2,3,6-tetrahydro-1λ⁶-[1,4]thiazin-3-yl)-4-fluoro-phenyl]-amide.

A certain embodiment of the invention provides a compound of formula I as described herein which is 5-Chloro-pyridine-2-carboxylic acid [3-((R)-5-amino-3-methyl-1,1-dioxo-1,2,3,6-tetrahydro-1λ⁶-[1,4]thiazin-3-yl)-4-fluoro-phenyl]-amide.

A certain embodiment of the invention provides a compound of formula I as described herein which is 5-Cyano-pyridine-2-carboxylic acid [3-((R)-9-amino-7-methyl-5,5-dioxo-5λ⁶-thia-8-aza-spiro[3.5]non-8-en-7-yl)-4-fluoro-phenyl]-amide.

A certain embodiment of the invention provides a compound of formula I as described herein which is 5-Chloro-pyridine-2-carboxylic acid [3-((R)-9-amino-7-methyl-5,5-dioxo-5λ⁶-thia-8-aza-spiro[3.5]non-8-en-7-yl)-4-fluoro-phenyl]-amide.

A certain embodiment of the invention provides a compound of formula I as described herein which is 5-Cyano-pyridine-2-carboxylic acid [3-((R)-10-amino-8-methyl-6,6-dioxo-6λ⁶-thia-9-aza-spiro[4.5]dec-9-en-8-yl)-4-fluoro-phenyl]-amide.

A process for preparing a compound of formula I as defined herein, which process comprises reacting a compound of formula XI with a compound of formula XII to a compound of formula I.

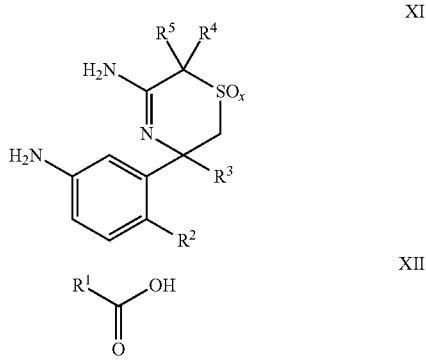

wherein x, R¹, R², R³, R⁴ and R⁵ are as defined herein.

A certain embodiment of the invention provides a compound of formula I as described herein, whenever prepared by a process as defined above.

A certain embodiment of the invention provides a compound of formula I as described herein for use as therapeutically active substance.

A certain embodiment of the invention provides a compound of formula I as described herein for the use as inhibitor of BACE1 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides a compound of formula I as described herein for the use in inhibition of BACE1 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use in the therapeutic and/or prophylactic treatment of Alzheimer's disease.

A certain embodiment of the invention provides a method for the use in inhibition of BACE1 activity, particularly for the therapeutic and/or prophylactic treatment of diseases and disorders characterized by elevated β-amyloid levels and/or β-amyloid oligomers and/or β-amyloid plaques and further deposits or Alzheimer's disease, which method comprises administering compound of formula I as described herein to a human being or animal.

A certain embodiment of the invention provides a method for the use in the therapeutic and/or prophylactic treatment of Alzheimer's disease, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I can exist in tautomeric form

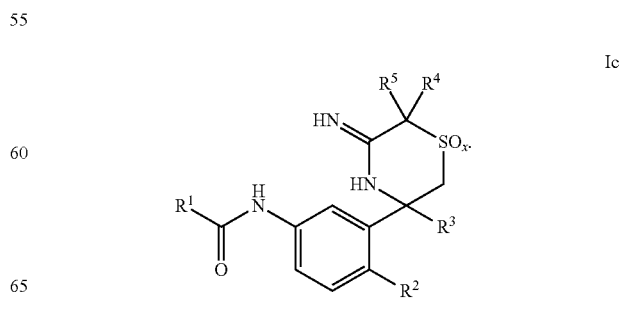

All tautomeric forms are encompassed in the present invention.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Stereoisomers of compounds of formula I are compounds of formula Ia or compounds of formula Ib, in particular compounds of formula Ia, wherein the residues have the meaning as described in any of the embodiments.

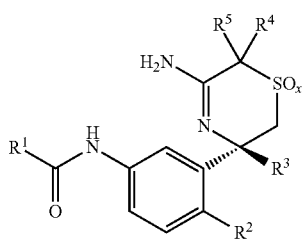

Ia

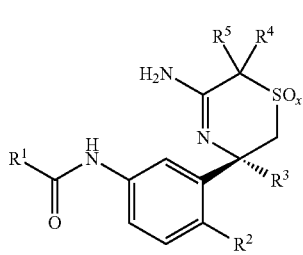

Ib

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula I may be prepared in accordance with the following schemes. The starting material is commercially available or may be prepared in accordance with known methods. Any previously defined residues and variables will continue to have the previously defined meaning unless otherwise indicated.

The compounds of formula I can be prepared through a number of synthetic routes for example as illustrated in schemes 1-5. The preparation of compounds of formula I of the present invention may be carried out in sequential or convergent synthetic routes. Syntheses of the compounds of the invention are shown in the following schemes 1-4. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes described below, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The compounds of formula I described in the schemes 1-5 can be isolated and purified by methods known to those skilled in the art, such as but not limited to ion exchange chromatography, solid phase extraction, liquid-liquid extraction, silica chromatography, crystallization and preparative HPLC.

In more detail, compounds of formula I according to the present invention can be prepared by the methods and procedures given below. Some typical procedures for the preparation of compounds of formula I are illustrated in Schemes 1-5.

Scheme 1: Synthesis of intermediate aminothiazines A15

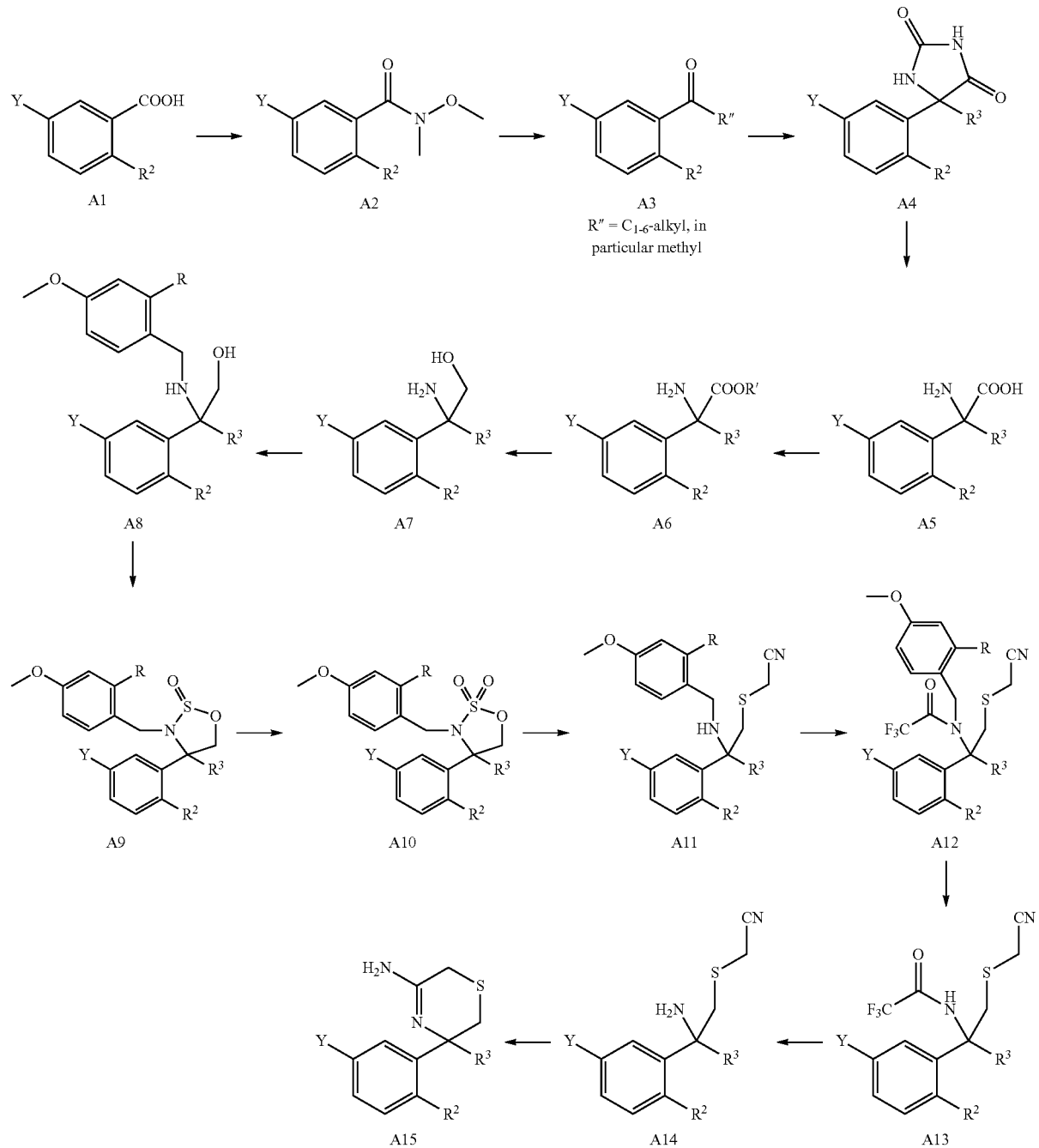

Non commercial ketones of general formula A3 can be synthesized by routes such as depicted in scheme 1 or by other routes known to those skilled in the art. Weinreb amides of formula A2 can be obtained by standard condensation reactions of the acids of formula A1 with N,O-dimethylhydroxylamine or by the intermediate formation of the acyl chloride of acids of formula A1 using an agent such as oxalyl chloride or thionyl chloride using standard conditions such as triethylamine/dichloromethane. The amides of formula A2 can be reacted with organometallics such as methylmagnesium bromide (for $R^3$=Me) in inert aprotic solvents such as tetrahydrofuran or diethyl ether to yield the desired ketones of formula A3.

According to scheme 1, ketones of general formula A3 (wherein Y has the meaning of a leaving group like halogen, e.g. bromide) can be reacted with cyanides, like potassium cyanide, together with ammonium carbonate in polar solvents such as alcohols, e.g. ethanol, water or tetrahydrofuran and mixtures thereof, to form hydantoins of formula A4. The hydantoin can then be treated with water along with a base such as sodium hydroxide or a strong acid such as sulfuric acid at temperatures ranging from ambient temperature to reflux to yield the amino acid of formula A5. The amino alcohol of formula A7 is obtained by esterification of the acid of formula A5 with a lower alcohol, such as methanol or ethanol, followed by reduction of the resulting amino ester of formula A6 with lithium aluminum hydride or other suitable reagents both steps performed under conditions known to those skilled in the art.

The amino alcohol of formula A7 can be reductively aminated to the N-benzylated aminoalcohol of formula A8 with an aldehyde, in particular p-methoxybenzaldehyde (R=H) or 2,4-dimethoxybenzaldehyde (R=OMe), using a reducing agent, in particular sodium cyanoborohydride or sodium triacetoxyborohydride, in a chlorinated solvent, in particular 1,2-dichloroethane or dichloromethane, in the presence of a weak organic acid, in particular acetic acid, at 0° C. to 60° C., in particular 23° C.

The N-benzylated aminoalcohol of formula A8 can be reacted with thionyl chloride to the cyclic sulfamidite of formula A9 in the presence of an amine base, in particular pyridine, in a chlorinated solvent, in particular dichloromethane, starting at low temperature such as −78° C. and warming up to 0° C. or ambient temperature.

The cyclic sulfamidite of formula A9 can be oxidized to the cyclic sulfamidate of formula A10 by an alkali periodate, such as sodium or potassium periodate, in the presence of a ruthenium salt, such as ruthenium(III) chloride, in solvent mixtures consisting of water, acetonitrile and ethyl acetate or tetrachloromethane at temperatures between 0° C. and 50° C., in particular at 23° C.

The cyclic sulfamidate of formula A10 can be regioselectively opened with a sulfur nucleophile, such as mercaptoacetonitrile, and subsequently hydrolyzed under acidic conditions to the N-benzylated amino nitrile of formula A11. The ring opening proceeds in the presence of an amine base, such as 1,8-diazabicyclo[5.4.0]undec-7-ene (DBU) or 1,1,3,3-tetramethylguanidine (TMG), in a polar aprotic solvent, such as N,N-dimethylformamide, at temperatures between 23° C. and 80° C., in particular at 60° C. After removal of all volatiles from the ring opening step under vacuum by evaporation the crude reaction mixture is subjected to acidic hydrolysis in a mixture of a mineral acid, in particular 20% aqueous sulfuric acid, and a solvent such as diethyl ether or dichloromethane at temperatures between 0° C. and 50° C., in particular at 23° C.

The N-benzylated amino nitrile of formula A11 is deprotected to the amino nitrile of formula A14 in a three-step protocol: first, the to the N-benzylated amino nitrile of formula A11 is reacted with an organic anhydride, in particular trifluoroacetic anhydride, in the presence of an amine base, in particular triethylamine or diisopropylethylamine, in a chlorinated solvent such as dichloromethane at temperatures between 0° C. and 40° C., in particular at 23° C. to give the N-benzylated N-trifluoroacetylated amino nitrile of formula A12. Second, the N-benzylated N-trifluoroacetylated amino nitrile of formula A12 is debenzylated to the N-trifluoroacetylated amino nitrile of formula A13 by neat reaction with a strong organic acid, in particular trifluoromethanesulfonic acid in trifluoroacetic acid, at temperatures between 0° C. and 50° C., in particular at 23° C. Third, the N-trifluoroacetylated amino nitrile of formula A13 is deacylated to the amino nitrile of formula A14 by treatment with a reducing agent, such as sodium borohydride, in an alcoholic solvent, in particular methanol or ethanol, at temperatures between 0° C. and 60° C., in particular at 23° C.

The amino nitrile of formula A14 can be cyclized to the aminothiazine of formula A15 using a Lewis acid such as trimethylaluminum in an inert solvent, in particular toluene, at temperatures from 23° C. to 100° C., in particular 60° C.

Scheme 2: Synthesis of compounds of formula I′

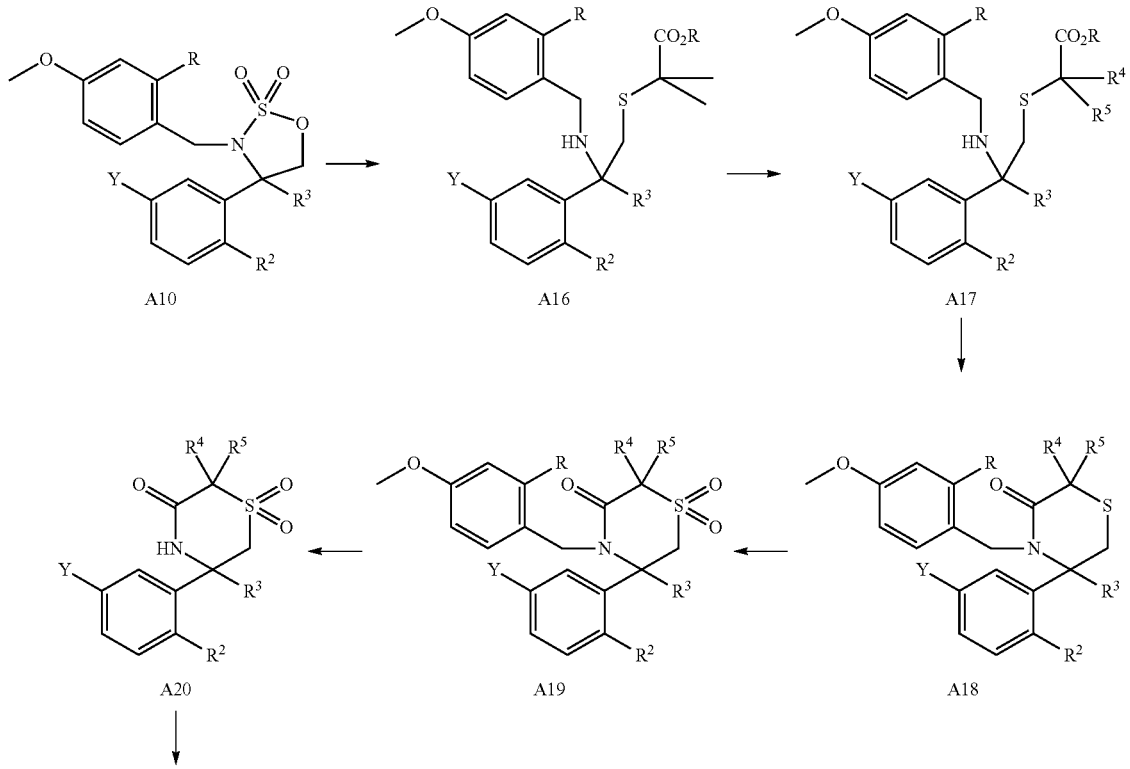

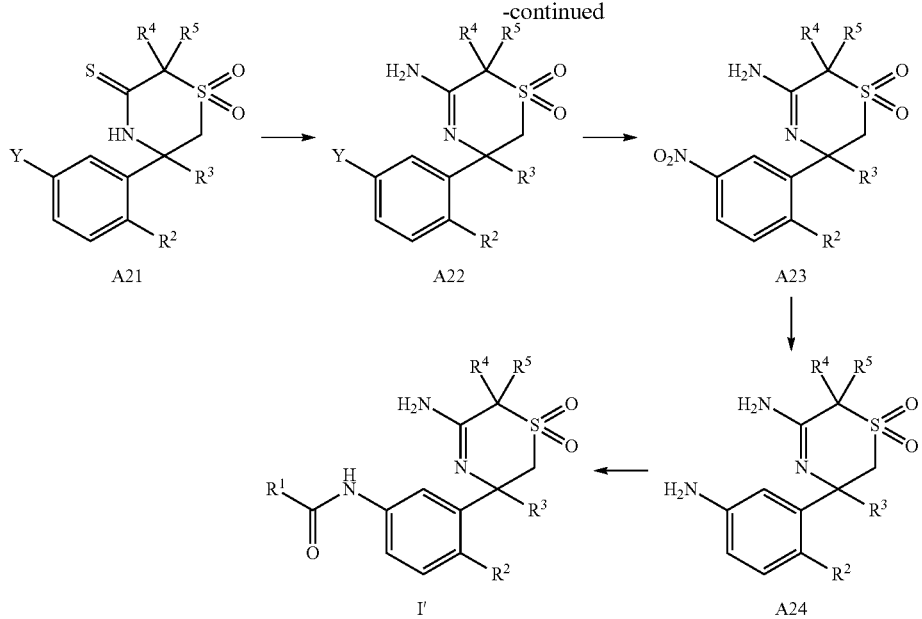

The cyclic sulfamidate of formula A10 can be regioselectively opened with a sulfur nucleophile, such as mercaptoaceticacid esters, and subsequently hydrolyzed under acidic conditions to the N-benzylated amino ester of formula A16. The ring opening proceeds in the presence of an amine base, such as 1,8-diazabicyclo[5.4.0]undec-7-ene (DBU) or 1,1,3,3-tetramethylguanidine (TMG), in a polar aprotic solvent, such as N,N-dimethylformamide, at temperatures between 23° C. and 80° C., in particular at 60° C. After removal of all volatiles from the ring opening step under vacuum by evaporation the crude reaction mixture is subjected to acidic hydrolysis in a mixture of a mineral acid, in particular 20% aqueous sulfuric acid, and a solvent such as diethyl ether or dichloromethane at temperatures between 0° C. and 50° C., in particular at 23° C.

The N-benzylated amino ester of formula A16 can be saponified to the N-benzylated amino acid of formula A17 by treatment with an alkali hydroxide, such as lithium, sodium or potassium hydroxide, in an aqueous alcoholic solvent, like e.g. methanol or ethanol, at temperatures between 23 and 100° C.

The N-benzylated amino acid of formula A11 can be cyclized to the N-benzylated lactam of formula A18 by treatment with the cyclic trimer of N-propylphosphonic acid (2,4,6-trioxo-2,4,6-tri-n-propyl-1,3,5,2,4,6-trioxatriphosphorinane; CAS-no 68957-94-8) in the presence of a base, in particular an alkylamine such as diisopropylethylamine (DIPEA) or triethylamine (TEA), or a tertiary amine such as N-methylmorpholine or 4-(dimethylamino)-pyridine. The reaction is carried out in a suitable solvent such as for example N,N-dimethylformamide (DMF), dimethylacetamide (DMAc), dichloromethane (DCM) or ethyl acetate (AcOEt), at temperatures between 0° C. and ambient temperature.

The thioether A18 can be oxidized to the sulfone A19 by treatment with an oxidizing reagent, in particular meta-chloroperbenzoic acid, in dichloromethane as a solvent at room temperature. Alternatively the oxidation can be carried out using potassium peroxymonosulfate (Oxone) in a solvent such as methanol at ambient temperature.

The N-benzylated lactam of formula A19 can be debenzylated to the β-sulfonyllactam of formula A20 by neat reaction with a strong organic acid, in particular trifluoromethanesulfonic acid in trifluoroacetic acid, at temperatures between 0° C. and 50° C., in particular at 23° C.

The β-sulfonyllactam of formula A20 can be converted into the thiolactam A21 by reaction with 2,4-bis-(4-methoxyphenyl)-[1,3,2,4]dithiadiphosphetane 2,4-disulfide (Lawesson's reagent) or phosphorous pentasulfide in an ether solvent such as THF, 1,2-dimethoxyethane or 1,4-dioxane, in particular 1,4-dioxane, at temperatures between 23 and 100° C., in particular between 50 and 80° C.

The β-sulfonylamidines of formula A22 can be prepared from the thiolactams of formula A21 by reaction with an solution of ammonia in a protic solvent such as methanol, ethanol or water, in particular methanol, with or without presence of a mild oxidant such as tert-butylhydroperoxide at temperatures between 0 and 60° C., in particular at 23° C. in the presence of an oxidant or at 50 to 60° C. in the absence of an oxidant.

If the β-sulfonylamidines of formula A22 contain Y=Br reduction to Y=H can be accomplished by hydrogenation using a catalyst such as Pd/C in protic solvents, such as alcohols, in particular ethanol or methanol, in particular in the presence of ammonium hydroxide, in particular at ambient temperature.

The nitration of the β-sulfonylamidines of formula A22 with Y=H to give the nitro-β-sulfonylamidine A23 follows a standard procedure involving neat sulfuric acid and fuming nitric acid without using a solvent at temperatures between 0° C. and 23° C.

The reduction of the nitro group in the nitro-β-sulfonylamidine A23 to give the aniline A24 can be accomplished by hydrogenation using a catalyst such as Pd/C in protic solvents, such as alcohols, in particular ethanol or methanol, at ambient temperature.

Selective amide coupling of the aniline A24 and a carboxylic acid to give the amide Ib can be effected with 4-(4,6-dimethoxy[1.3.5]triazin-2-yl)-4-methylmorpholinium chloride (DMTMM) hydrate in a solvent such as an alcohol, in particular methanol, at ambient temperature.

Scheme 3: Alternative synthesis of compounds of formula I'

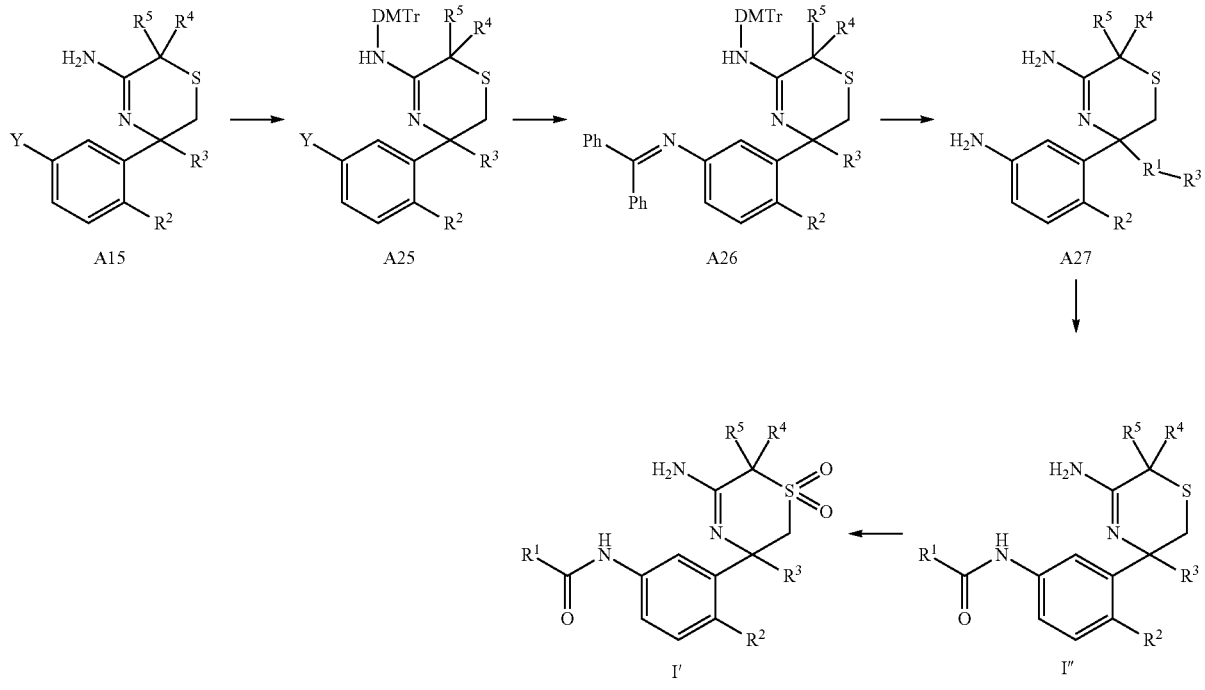

$R^4/R^5 = H$

Protection of the amino group in compounds of formula A15, to produce aryl bromides of formula A25 can be performed with triarylmethyl chlorides, such as triphenylmethyl chloride (Tr-Cl), p-methoxyphenyldiphenylmethyl chloride (MMTr-Cl), di(p-methoxyphenyl)phenylmethyl chloride (DMTr-Cl) or tri(p-methoxyphenyl)methyl chloride (TMTr-Cl), in particular DMTr-Cl, under basic conditions, e.g. in the presence of an amine, such as triethylamine or diisopropylethylamine, in a chlorinated solvent, such as dichloromethane or chloroform, at temperatures between 0° C. and ambient temperature.

Aryl bromides of formula A25 can be reacted with ammonia equivalents, such as benzophenone imine, in the presence of a suitable transition metal catalyst, such as bis(dibenzylideneacetone)palladium (0) ((dba)$_2$Pd) or tris(dibenzylideneacetone)dipalladium (0) ((dba)$_3$Pd$_2$)), and a suitable ligand, such as rac-2,2'-bis(diphenylphosphino)-1,1'-binaphthyl (rac-BINAP), 2-dicyclohexylphosphino-2',4',6'-triisopropylbiphenyl (X-PHOS) or 2-di-tert-butylphosphino-2',4',6'-triisopropylbiphenyl (t-Bu X-PHOS), in the presence of a base, such as sodium tert-butoxide, potassium phosphate or cesium carbonate, in a suitable solvent, such as toluene or 1,4-dioxane, under an inert atmosphere, such as nitrogen or argon, at temperatures between 80 and 110° C., to produce compounds of formula A26.

Deprotection of both amino groups in compounds of formula A26 can be achieved by a one-pot procedure by first reacting it with a strong organic acid, such as trifluoroacetic acid, in chlorinated solvents, such as dichloromethane or chloroform, under anhydrous conditions at temperatures between 0° C. and ambient temperature to cleave the P'-group. Then the addition of water or aqueous hydrochloric acid to cleave the benzophenone imine and reaction at ambient temperature produces diamines of formula A27.

Selective amide coupling of the aniline A27 and a carboxylic acid to give the amide I'' can be effected with 4-(4,6-dimethoxy[1.3.5]triazin-2-yl)-4-methylmorpholinium chloride (DMTMM) hydrate in a solvent such as an alcohol, in particular methanol.

The thioether I'' can be oxidized to the sulfone I' by treatment with an oxidizing reagent, in particular meta-chloroperbenzoic acid, in dichloromethane as a solvent at room temperature.

Scheme 4: Alternative synthesis of intermediate amino alcohols of formula A7.

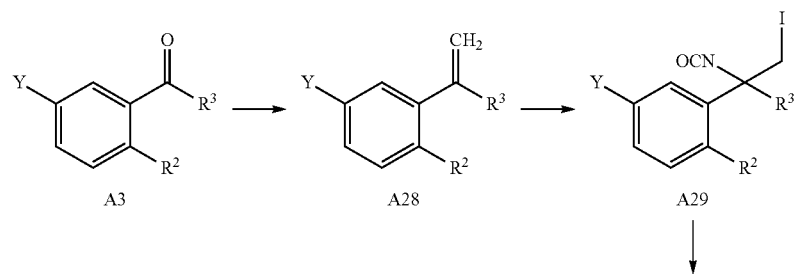

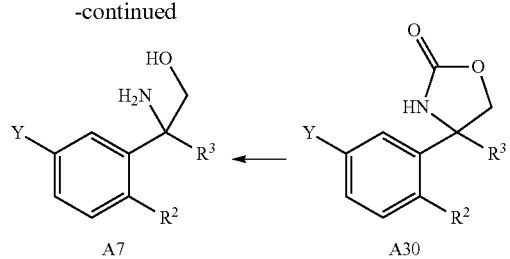

Alternatively, intermediate amino alcohols of formula A7 can be obtained as follows: According to scheme 4, the formation of a methyltriphenyl-phosphonium ylide produced by strong base such as butyllithium in solvents such as tetrahydrofuran or toluene at temperatures between −78° C. and 0° C. followed by addition of the ketone of formula A3 yields the desired alkenes of formula A28. The alkenes can then be reacted with a mixture of silver cyanate and iodine in solvents such as diethyl ether or mixtures of ethyl acetate and acetonitrile. The resultant iodoisocyanates of formula A29 can then be heated with alcohols like tert-butanol and a base like triethylamine or Huenig's base to yield the oxazolidinones of formula A30. Hydrolysis of the resultant oxazolidinone of formula A30 with aqueous base like lithium hydroxide yields the amino alcohol of formula A7.

directing group as described by Tang & Ellman or by A. Avenoza, J. H. Busto, F. Corzana, J. M. Peregrina, D. Sucunza, M. M. Zurbano in Synthesis 2005, (4), 575-578. The sulfinyl imine of formula A31 can be treated with an mixed alkyl alkoxide aluminum cyanide reagent, e.g. ethylaluminium cyanoisopropoxide [EtAl(O-i-Pr)CN], in a solvent such as an ether, e.g. diethyl ether or more particular tetrahydrofuran, at temperatures starting from −78° C. and eventually raising to −10° C., to generate the nitriles of formula A32 as described e.g. by A. Avenoza, J. H. Busto, F. Corzana, J. M. Peregrina, D. Sucunza, M. M. Zurbano in Synthesis 2005, (4), 575-578.

Hydrolysis of the chiral directing group in the nitriles of formula A32 to give first the chiral amino nitriles can be accomplished with a mineral acid, e.g. sulfuric acid or in Scheme 5: Enantioselective synthesis of intermediate amino alcohols of formula A7.

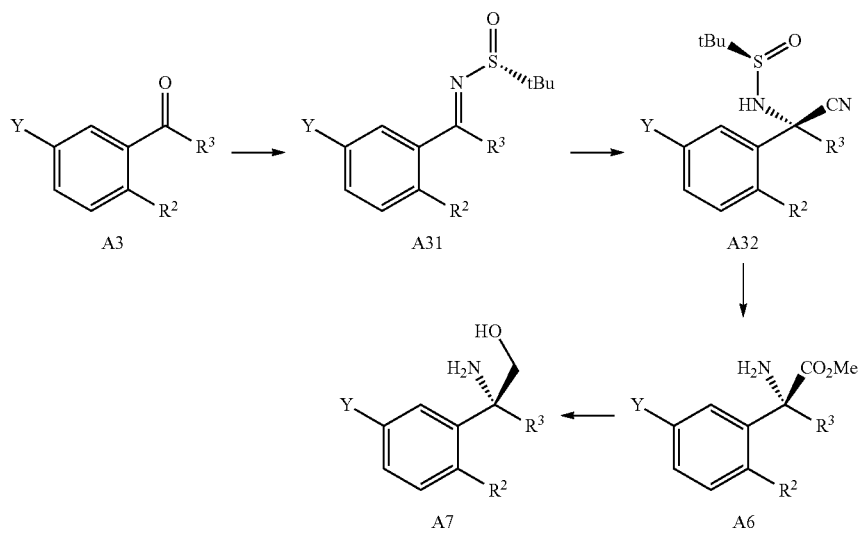

R3 = $C_{1-6}$alkyl

Intermediate amino alcohols of formula A7 can be prepared in an enantioselective manner as follows: aromatic ketones of formula A3 can be converted into the sulfinyl imine of general formula A31 in analogy to T. P. Tang & J. A. Ellman, J. Org. Chem. 1999, 64, 12, by condensation of the aryl ketone group and a sulfinamide, e.g. an alkyl sulfinamide, in this case most in particular (R)-(+)-tert-butylsulfinamide in the presence of a Lewis acid such as e.g. a titanium(IV) alkoxide, more particular titanium(IV)ethoxide in a solvent such as an ether, e.g. diethyl ether or more particular tetrahydrofuran, at temperatures between 23° C. and 70° C.

The conversion of the sulfinyl imine of formula A31 to the nitrile of formula A32 proceeds stereoselectively by the chiral particular hydrochloric acid in a solvent such as an ether, e.g. diethyl ether, tetrahydrofuran or more particular 1,4-dioxane, which is followed by another acidic reaction with a mineral acid, e.g. anhydrous hydrochloric acid or in particular sulfuric acid in a solvent such as an aliphatic alcohol, e.g. ethanol or more particular methanol, at temperatures from 23° C. to 80° C., to give the chiral amino esters of formula A6.

Also chiral amino esters of formula A6 can be reduced to the chiral amino alcohols of formula A7 by reaction with a reducing agent such as e.g. lithium borohydride or more particular lithium aluminum hydride in an ether solvent, like e.g. diethyl ether or more particular THF, at temperatures between 0° C. and 50° C., in particular at 23° C.

The corresponding pharmaceutically acceptable salts with acids can be obtained by standard methods known to the person skilled in the art, e.g. by dissolving the compound of formula I in a suitable solvent such as e.g. dioxan or tetrahydrofuran and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. M(OH)$_n$ wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate. Specific is hydrochloride.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention may be derivatised at functional groups to provide derivatives which are capable of conversion back to the parent compound in vivo.

Pharmacological Tests

The compounds of formula I and their pharmaceutically acceptable salts possess valuable pharmacological properties. It has been found that the compounds of the present invention are associated with inhibition of BACE1 activity. The compounds were investigated in accordance with the test given hereinafter.

Cellular Aβ-Lowering Assay:

The Abeta 40 AlphaLISA Assay can be used. The HEK293 APP cells were seeded in 96 well Microtiter plates in cell culture medium (Iscove's, plus 10% (v/v) fetal bovine serum, penicillin/streptomycin) to about 80% confluency and the compounds were added at a 3× concentration in ⅓ volume of culture medium (final DMSO concentration was kept at 1% v/v). After 18-20 hrs incubation at 37° C. and 5% $CO_2$ in a humidified incubator, the culture supernatants were harvested for the determination of Aβ 40 concentrations using Perkin-Elmer Human Amyloid beta 1-40 (high specificity) Kit (Cat#AL275C).

In a Perkin-Elmer White Optiplate-384 (Cat#6007290), 2 ul culture supernatants were combined with 2 µl of a 10× AlphaLISA Anti-hAβAcceptor beads+Biotinylated Antibody Anti-Aβ 1-40 Mix (50 µg/mL/5 nM). After 1 hour room temperature incubation, 16 µl of a 1.25× preparation of Streptavidin (SA) Donor beads (25 µg/mL) were added and incubated for 30 minutes in the Dark. Light Emission at 615 nm was then recorded using EnVision-Alpha Reader. Levels of Aβ 40 in the culture supernatants were calculated as percentage of maximum signal (cells treated with 1% DMSO without inhibitor). The IC50 values were calculated using the Excel XLfit software.

TABLE 1

$IC_{50}$ values of selected examples

| Exam. | Structure | BACE1 cell act. Aβ40, $IC_{50}$ [nM] |
|---|---|---|
| 1 | 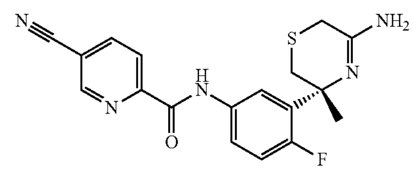 [SMILES: C[C@@]1(c2cc(NC(=O)c3ccc(C#N)cn3)ccc2F)CSCC(N)=N1] | 0.011 |
| 2 | 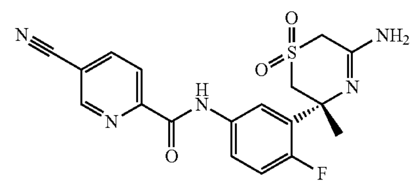 [SMILES: C[C@@]1(c2cc(NC(=O)c3ccc(C#N)cn3)ccc2F)CS(=O)(=O)CC(N)=N1] | 0.0082 |
| 3 | 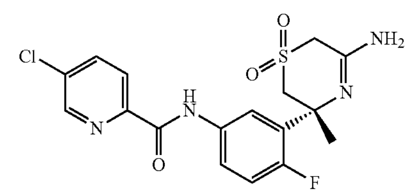 [SMILES: C[C@@]1(c2cc(NC(=O)c3ccc(Cl)cn3)ccc2F)CS(=O)(=O)CC(N)=N1] | 0.0061 |
| 4 | 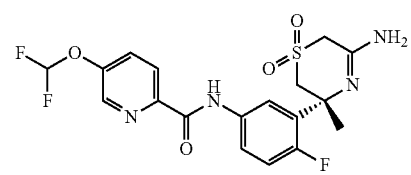 [SMILES: C[C@@]1(c2cc(NC(=O)c3ccc(OC(F)F)cn3)ccc2F)CS(=O)(=O)CC(N)=N1] | 0.0057 |
| 5 | 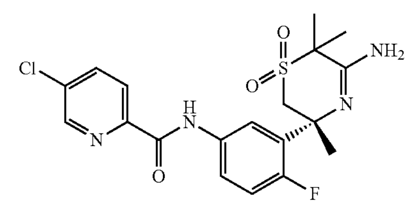 [SMILES: CC1(C)C(N)=N[C@](C)(c2cc(NC(=O)c3ccc(Cl)cn3)ccc2F)CS1(=O)=O] | 0.0009 |
| 6 | 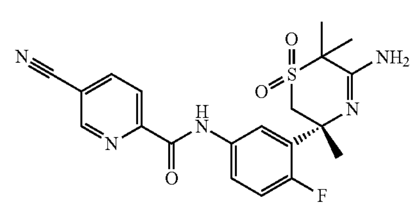 [SMILES: CC1(C)C(N)=N[C@](C)(c2cc(NC(=O)c3ccc(C#N)cn3)ccc2F)CS1(=O)=O] | 0.0002 |
| 7 | 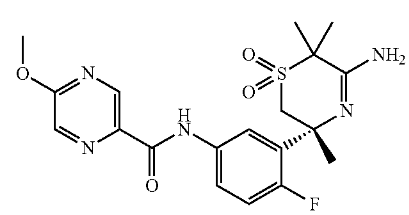 [SMILES: COc1cnc(C(=O)Nc2ccc(F)c([C@]3(C)CS(=O)(=O)C(C)(C)C(N)=N3)c2)cn1] | 0.0009 |

TABLE 1-continued

IC$_{50}$ values of selected examples

| Exam. | Structure | BACE1 cell act. Aβ40, IC$_{50}$ [nM] |
|---|---|---|
| 8 | 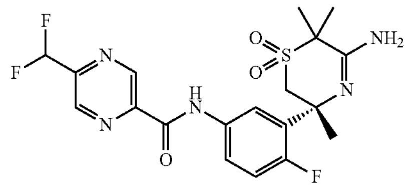 [SMILES: CC1(C)C(N)=N[C@](C)(c2cc(NC(=O)c3cnc(C(F)F)cn3)ccc2F)CS1(=O)=O] | 0.0018 |
| 9 | 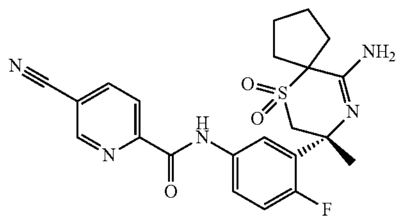 [SMILES: C[C@@]1(c2cc(NC(=O)c3ccc(C#N)cn3)ccc2F)CS(=O)(=O)C2(CCCC2)C(N)=N1] | 0.001 |
| 10 | 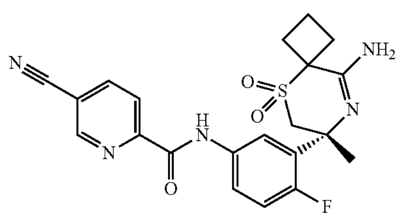 [SMILES: C[C@@]1(c2cc(NC(=O)c3ccc(C#N)cn3)ccc2F)CS(=O)(=O)C2(CCC2)C(N)=N1] | |
| 11 | 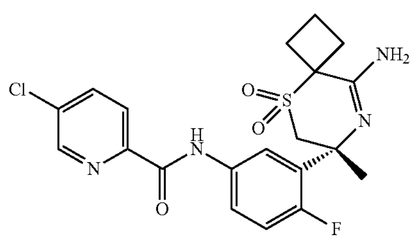 [SMILES: C[C@@]1(c2cc(NC(=O)c3ccc(Cl)cn3)ccc2F)CS(=O)(=O)C2(CCC2)C(N)=N1] | |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

General:

NMR: $^1$H NMR spectra were recorded on a Bruker AC-300 spectrometer at 25° C. with TMS (tetramethylsilane) or residual $^1$H of the given deuterated solvents as internal standards.

MS: Mass spectra (MS) were measured either with ion spray positive or negative (ISP or ISN) method on a Perkin-Elmer SCIEX API 300, or by electrospray on a single quadrupole mass spectrometer from Applied Biosystem (API150) or with electron impact method (EI, 70 eV) on a Finnigan MAT SSQ 7000 spectrometer.

Synthesis of Intermediates A4

A4a: (RS)-5-(3-Bromo-phenyl)-5-methyl-imidazolidine-2,4-dione

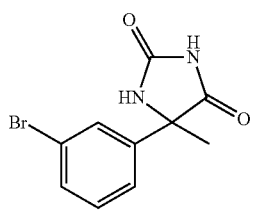

A mixture of 3-bromo-acetophenone (10.0 g, 50 mmol), potassium cyanide (4.96 g, 75 mmol), and ammonium carbonate (33.45 g, 348 mmol) in ethanol (65 ml) was heated in an autoclave at 120° C. for 16 h. For the workup, the reaction mixture was cooled to room temperature, and then treated with water (250 ml) and ethyl acetate (500 ml). The aqueous layer was separated and re-extracted with ethyl acetate (250 ml). The combined organic layers were washed twice with saturated sodium chloride solution (2×250 ml), thereafter dried over sodium sulfate, and evaporated at reduced pressure. There were obtained 13.2 g (98.6% of theory) of (RS)-5-(3-bromo-phenyl)-5-methyl-imidazolidine-2,4-dione as a white solid. The purity of the product allowed using it in the next step without further purification. Mass (calculated) $C_{10}H_9BrN_2O_2$ [269.099]; (found) [M−H]$^−$=267, 269.

A4b: (RS)-5-(5-Bromo-2-fluoro-phenyl)-5-methyl-imidazolidine-2,4-dione

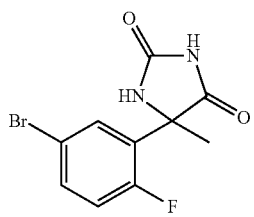 [SMILES: CC1(c2cc(Br)ccc2F)NC(=O)NC1=O]

The reaction of commercially available 1-(5-bromo-2-fluoro-phenyl)-ethanone with potassium cyanide and ammonium carbonate in ethanol in an autoclave at 120° C. for 16 h yielded the title compound as light yellow solid. Mass (calculated) $C_{10}H_8BrFN_2O_2$ [287.087]; (found) [M−H]$^−$=285, 287.

A4c: (RS)-5-(2-Fluoro-phenyl)-5-methyl-imidazolidine-2,4-dione

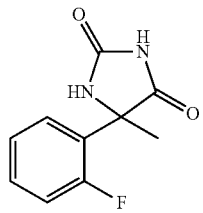

A mixture of freshly distilled 1-(2-fluorophenyl)ethanone (27.6 g, 24.6 ml, 200 mmol, Eq: 1.00), potassium cyanide (15.6 g, 240 mmol, Eq: 1.20), ammonium carbonate (96.1 g, 1.00 mol, Eq: 5.00) and ammonium hydroxide (25%) (130 g, 145 ml, 931 mmol, Eq: 4.65) in ethanol (250 ml) and water (200 ml) was stirred at 60° C. for 5.5 h. The ethanol was removed in vacuum, then cooled to 0° C., cautiously acidified the residue to pH 1, the precipitate was filtered off, washed with dilute HCl and dried at 50° C. first at rotary evaporator, then at high vacuum to give the 5-(2-fluorophenyl)-5-methylimidazolidine-2,4-dione (40.4 g, 194 mmol, 97.0% yield) as a white solid. MS (ISN): m/z=207.5 [M−H]$^−$.

Synthesis of Intermediates A6

A6a: (RS)-2-Amino-2-(3-bromo-phenyl)-propionic acid methyl ester

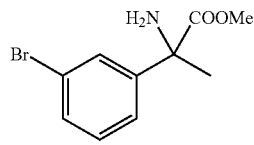

A dispersion of (RS)-5-(3-bromo-phenyl)-5-methyl-imidazolidine-2,4-dione (12.81 g, 48 mmol) in 6 N sodium hydroxide solution (95.23 ml) was heated to reflux for 48 h. For the workup, the reaction mixture was cooled with ice and treated with hydrochloric acid (36.5%) until pH 1 was reached. The mixture was evaporated to dryness at reduced pressure. The crude (RS)-2-amino-2-(3-bromo-phenyl)-propionic acid hydrochloride was dispersed in methanol (500 ml) and cooled to 0° C. Within 12 minutes and under ice cooling, thionylchloride (18.02 ml, 246 mmol) was added dropwise. After complete addition, the reaction mixture was heated to reflux for 60 h. For the workup, the reaction mixture was cooled to room temperature and evaporated at reduced pressure. The white residue was treated with a mixture of water and ice (200 ml), triethylamine (16.5 ml), and diethyl-ether (500 ml). The resulting suspension was filtrated over Dicalit; thereafter the aqueous layer was separated and re-extracted with diethylether (250 ml). The combined organic layers were washed with saturated sodium chloride solution (250 ml), dried over sodium sulfate, and evaporated at reduced pressure. There were obtained 9.39 g (76.7% of theory) of (RS)-2-amino-2-(3-bromo-phenyl)-propionic acid methyl ester as a light yellow oil. The purity of the product allowed using it in the next step without further purification. Mass (calculated) $C_{10}H_{12}BrNO_2$ [258.117]; (found) $[M+H]^+$ =258, 260.

A6b: (RS)-2-Amino-2-(5-bromo-2-fluoro-phenyl)-propionic acid methylester

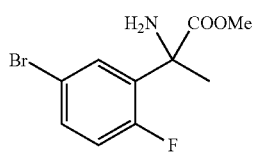

The hydrolysis of the (RS)-5-(5-bromo-2-fluoro-phenyl)-5-methyl-imidazolidine-2,4-dione with 6 N sodium hydroxide solution and esterification of the resulting (RS)-2-amino-2-(5-bromo-2-fluoro-phenyl)-propionic acid with methanol and thionylchloride yielded the (RS)-2-amino-2-(5-bromo-2-fluoro-phenyl)-propionic acid methylester as a light yellow oil. The purity of the product allowed using it in the next step without further purification. Mass (calculated) $C_{10}H_{11}BrFNO_2$ [276.107]; (found) $[M+H]^+$=276, 278.

A6c: (RS)-2-Amino-2-(2-fluoro-phenyl)-propionic acid methylester

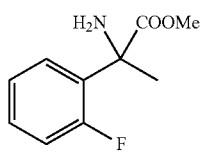

The hydrolysis of the (RS)-5-(2-fluoro-phenyl)-5-methyl-imidazolidine-2,4-dione with 3 N sodium hydroxide solution and esterification of the resulting (RS)-2-amino-2-(2-fluoro-phenyl)-propionic acid with methanol and thionylchloride yielded the (RS)-2-amino-2-(2-fluoro-phenyl)-propionic acid methylester as a light yellow liquid. The purity of the product allowed using it in the next step without further purification. MS (ISP): m/z=198.2 $[M+H]^+$.

A6d: (R)-2-Amino-2-(5-bromo-2-fluoro-phenyl)-propionic acid methyl ester

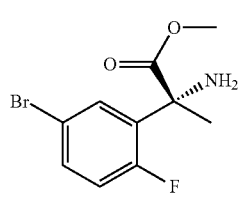

A mixture of (R)—N—((R)-1-(5-bromo-2-fluorophenyl)-1-cyano ethyl)-2-methylpropane-2-sulfinamide (8.869 g, 25.54 mmol) in conc. hydrochloric acid (90 ml, 1078 mmol) was stirred at 23° C. for 4 h, then cooled to 0° C. and treated with 32% sodium hydroxide solution (120 ml, 1277 mmol), diluted with water (100 ml) and extracted with ethyl acetate (1×300 ml and 2×200 ml). The combined organic layers were dried over $Na_2SO_4$, filtered and the solvent was removed in vacuum to leave the amide as an off-white solid. Dissolved in methanol (100 ml) and cautiously added conc. sulfuric acid (21.39 ml, 383 mmol), the mixture was stirred at reflux for 40 h, cooled to 0° C. and neutralized with sat. $Na_2CO_3$-sol. until pH 9 was reached. Extracted with ethyl acetate (3×100 ml), the combined organic layers were dried over $Na_2SO_4$, filtered and the solvent was removed in vacuum to give the (R)-methyl 2-amino-2-(5-bromo-2-fluorophenyl)propanoate (5.17 g, 73%) as a light yellow oil which was used without further purification. MS (ISP): m/z=276.1 $[M+H]^+$ and 278.0 $[M+2+H]^+$.

Synthesis of Intermediates A7

A7a: (RS)-2-Amino-2-(3-bromo-phenyl)-propan-1-ol

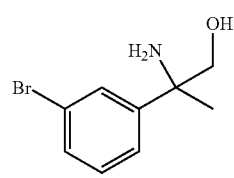

A solution of the (RS)-2-amino-2-(3-bromo-phenyl)-propionic acid methyl ester (9.39 g, 36 mmol) in tetrahydrofuran (360 ml) was treated portionwise at −5° C. with lithiumaluminiumhydride (1.41 g, 36 mmol; 282 mg/2 min). After complete addition, stirring was continued at 0-5° C. for 30 minutes. For the workup, the reaction mixture was cooled to −7° C., and water (9 ml) was added dropwise. Thereafter, 2 N sodium hydroxide solution (9 ml) was added and stirring continued for 15 minutes at room temperature. They grey suspension was filtrated through Dicalite which was washed with tetrahydrofuran (200 ml). The filtrate was evaporated at reduced pressure. There were obtained 8.67 g of crude (RS)-2-amino-2-(3-bromo-phenyl)-propan-1-ol as colorless oil. The purity of the product allowed using it in the next step without further purification. Mass (calculated) $C_9H_{12}BrNO$ [230.106]; (found) $[M+H]^+$=230, 232.

A7b: (RS)-2-Amino-2-(5-bromo-2-fluoro-phenyl)-propan-1-ol

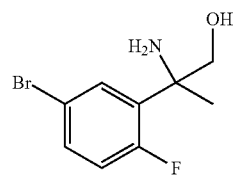

The reduction of the (RS)-2-amino-2-(5-bromo-2-fluoro-phenyl)-propionic acid methylester with lithiumaluminiumhydride in tetrahydrofuran yielded the (RS)-2-amino-2-(5-bromo-2-fluoro-phenyl)-propan-1-ol as a light yellow oil.

The purity of the product allowed using it in the next step without further purification. Mass (calculated) C₉H₁₁BrFNO [248.097]; (found) [M+H]⁺=248, 250.

A7c: (RS)-2-Amino-2-(2-fluoro-phenyl)-propan-1-ol

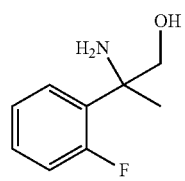

The reduction of the (RS)-2-amino-2-(2-fluoro-phenyl)-propionic acid methylester with lithiumaluminiumhydride in diethyl ether yielded the (RS)-2-amino-2-(2-fluoro-phenyl)-propan-1-ol as a light yellow oil. The purity of the product allowed using it in the next step without further purification. MS (ISP): m/z=170.3 [M+H]⁺.

A7d: (R)-2-Amino-2-(5-bromo-2-fluorophenyl)propan-1-ol

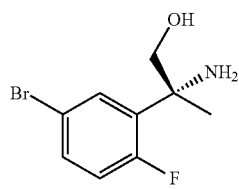

To a solution of (R)-methyl 2-amino-2-(5-bromo-2-fluorophenyl)propanoate (3.95 g, 14.3 mmol, Eq: 1.00) in diethyl ether (120 ml) was added at 0° C. lithium aluminum hydride (652 mg, 17.2 mmol, Eq: 1.2) in five portions. The icebath was removed and stirring continued at room temperature for 2 hours. To the cooled reaction mixture was added dropwise water (652 mg, 652 µl, 36.2 mmol, Eq: 2.53), NaOH (15% in water) (572 mg, 652 µl, 14.3 mmol, Eq: 1.00) and water (1.96 g, 1956 µl, 109 mmol, Eq: 7.59) via syringe (1:1:3 system) and the mixture was stirred for 20 min until a white suspension occurred. Three small spoons of Na₂SO₄ were added to the mixture, which was filtered after 5 min. The colourless ether solution was evaporated to give (R)-2-amino-2-(5-bromo-2-fluorophenyl)propan-1-ol (3.2 g, 12.9 mmol, 90.2% yield) as a white solid which was used in the next step without further purification. MS (ISP): m/z=248.1 [M+H]⁺ and 250.0 [M+2+H]⁺.

Synthesis of Intermediates A8

A8a: (R)-2-(5-Bromo-2-fluoro-phenyl)-2-(4-methoxy-benzylamino)-propan-1-ol

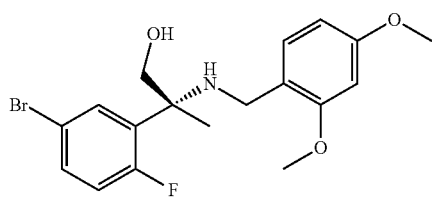 [SMILES: COc1ccc(CN[C@@](C)(CO)c2cc(Br)ccc2F)c(OC)c1]

To a solution of (R)-2-amino-2-(5-bromo-2-fluorophenyl) propan-1-ol (9.2 g, 37.1 mmol, Eq: 1.00) in 1,2-dichloroethane (145 ml) was added at 23° C. 2,4-dimethoxybenzaldehyde (6.16 g, 37.1 mmol, Eq: 1) followed by sodium triacetoxyborohydride (15.7 g, 74.2 mmol, Eq: 2.0). The reaction mixture was stirred at 23° C. overnight. The reaction mixture was extracted with sat NaHCO₃/CH₂Cl₂ twice. The combined organic layers were dried over Na₂SO₄, filtered off and evaporated totally. The residue was purified by silica gel chromatography with 0-50% EtOAc in heptane to give the (R)-2-(5-bromo-2-fluorophenyl)-2-(2,4-dimethoxybenzylamino)propan-1-ol (14.1 g, 35.4 mmol, 95.5% yield) as a light brown oil. Mass (calculated) C₁₈H₂₁BrFNO₃ [398.27]; (found) [M+H]⁺=398.0, 400.0.

Synthesis of Intermediates A9

A9a: (R)-4-(5-Bromo-2-fluoro-phenyl)-3-(2,4-dimethoxy-benzyl)-4-methyl-[1,2,3]oxathiazolidine 2-oxide

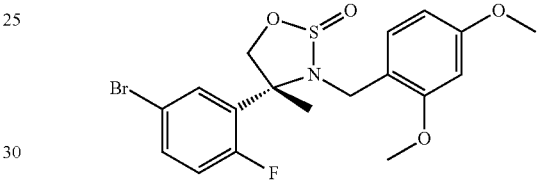

To a solution of (R)-2-(5-bromo-2-fluorophenyl)-2-(2,4-dimethoxybenzylamino)propan-1-ol (14.1 g, 35.4 mmol, Eq: 1.00) and pyridine (14.0 g, 14.3 ml, 177 mmol, Eq: 5.0) in dichloromethane (258 ml) at 78° C. was dropwise added thionyl chloride (5.05 g, 3.1 ml, 42.5 mmol, Eq: 1.2), stirring was continued at 78° C. for 5 min, the cooling bath was removed and the mixture was slowly warmed up to 23° C. and stirring was continued for 20 min. Extracted with 5% citric acid and sat NaHCO₃-sol., dried the organic layer over Na₂SO₄, filtered off and evaporated totally to give the (R)-4-(5-bromo-2-fluoro-phenyl)-3-(2,4-dimethoxy-benzyl)-4-methyl-[1,2,3]oxathiazolidine 2-oxide (15.7 g, 35.3 mmol, 99.8% yield) as a light yellow oil, which needed no further purification. MS (ISP): m/z=444.1 [M+H]⁺ and 446.0 [M+2+H]⁺.

Synthesis of Intermediates A10

A10a: (R)-4-(5-Bromo-2-fluoro-phenyl)-3-(2,4-dimethoxy-benzyl)-4-methyl-[1,2,3]oxathiazolidine 2,2-dioxide

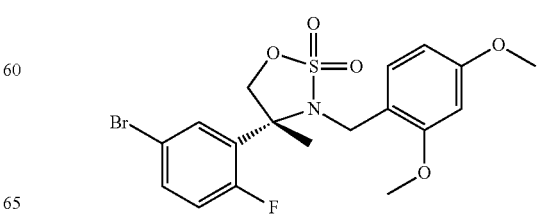

To a mixture of (R)-4-(5-bromo-2-fluoro-phenyl)-3-(2,4-dimethoxy-benzyl)-4-methyl-[1,2,3]oxathiazolidine 2-oxide (15.7 g, 35.3 mmol, Eq: 1.00) and sodium periodate (8.31 g, 38.9 mmol, Eq: 1.1) in ethyl acetate (120 ml), acetonitrile (120 ml) and cold water (192 ml) at 23° C. was added ruthenium(III) chloride (73.3 mg, 353 µmol, Eq: 0.01) and this reaction mixture was stirred vigorously at 23° C. for 30 minutes. Extracted with sat NaHCO$_3$, ethyl acetate, dried the organic layer over Na$_2$SO$_4$, filtered off and evaporated totally. The residue was purified by silica gel column chromatography with heptane/ethyl acetate to give the. The product fractions were collected and totally evaporated, dried in HV to give the (R)-4-(5-bromo-2-fluoro-phenyl)-3-(2,4-dimethoxy-benzyl)-4-methyl-[1,2,3]oxathiazolidine 2,2-dioxide (15.6 g, 33.9 mmol, 95.9% yield) as a white solid. MS (ISN): m/z=458.0 [M−H]$^-$ and 460.0 [M+2H]$^-$.

Synthesis of Intermediates A11

A11a: (R)-2-(2-(5-Bromo-2-fluorophenyl)-2-(2,4-dimethoxybenzylamino)propylthio)acetonitrile

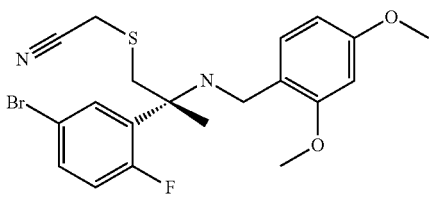 [SMILES: COc1ccc(CN[C@@](C)(CSCC#N)c2cc(Br)ccc2F)c(OC)c1]

a) 2-Mercaptoacetonitrile: To a solution of commercially available S-cyanomethyl ethanethioate [59463-56-8] (28.4 g, 247 mmol, Eq: 1.00) in methanol (280 ml) under argon was added Amberlyst® 15 (10.7 g, 247 mmol, Eq: 1.00). The mixture was stirred at reflux (70° C.) overnight. The cooled reaction mixture was filtered into a round bottom flask containing 2 g of Amberlyst® 15 for stabilization. Then the solvent was evaporated in vacuum at ambient temperature leaving the 2-mercaptoacetonitrile (14.35 g, 196 mmol, 79.6% yield) as a dark brown liquid.

b) To a solution of (R)-4-(5-Bromo-2-fluoro-phenyl)-3-(2,4-dimethoxy-benzyl)-4-methyl-[1,2,3]oxathiazolidine 2,2-dioxide (5.1 g, 11.1 mmol, Eq: 1.00) and 1,1,3,3-tetramethylguanidine (1.91 g, 2.09 ml, 16.6 mmol, Eq: 1.5) in DMF (77.3 ml) was added at 23° C. 2-mercaptoacetonitrile (1.22 g, 16.6 mmol, Eq: 1.5) dropwise. The reaction mixture was stirred at 23° C. for 16 hours. All volatiles were was evaporated at high vacuum and the resulting residue was stirred vigorously between 60 ml of dichloromethane and 20% (v/v) sulfuric acid solution (60 ml) for 40 hours. Sat. NaHCO$_3$ solution was slowly added (pH=8), then extracted twice with dichloromethane. The combined organic layers were dried over Na$_2$SO$_4$, filtered and evaporated. The residue was purified by silica gel column chromatography with 0-50% ethyl acetate in heptane to give (R)-2-(2-(5-bromo-2-fluorophenyl)-2-(2,4-dimethoxybenzylamino)propylthio)acetonitrile (5.2 g, 10.9 mmol, 98.3% yield) as a light brown oil. MS (ISP): m/z=453.0 [M+H]$^+$ and 455.2 [M+2+H]$^+$.

Synthesis of Intermediates A12

A12a: (R)—N-(2-(5-Bromo-2-fluorophenyl)-1-(cyanomethylthio)propan-2-yl)-N-(2,4-dimethoxybenzyl)-2,2,2-trifluoroacetamide

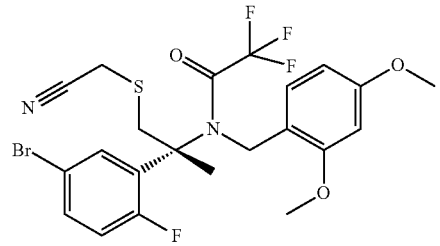 [SMILES: COc1ccc(CN(C(=O)C(F)(F)F)[C@@](C)(CSCC#N)c2cc(Br)ccc2F)c(OC)c1]

To a solution of (R)-2-(2-(5-bromo-2-fluorophenyl)-2-(2,4-dimethoxybenzylamino) propylthio)acetonitrile (5.2 g, 11.5 mmol, Eq: 1.00) and triethylamine (2.32 g, 3.2 ml, 22.9 mmol, Eq: 2.0) in dichloromethane (30 ml) was added at 0° C. trifluoroacetic anhydride (3.61 g, 2.43 ml, 17.2 mmol, Eq: 1.5) in dichloromethane (5 ml) dropwise. The reaction mixture was stirred at 0° C. for 20 min, then at 23° C. for 2 hours. Extracted with water and dichloromethane, dried the organic layer over Na$_2$SO$_4$, filtered off and evaporated totally. The residue was purified by silica gel column chromatography with 0 to 50% ethyl acetate in heptane to give the (R)—N-(2-(5-bromo-2-fluorophenyl)-1-(cyanomethylthio)propan-2-yl)-N-(2,4-dimethoxybenzyl)-2,2,2-trifluoroacetamide (5.9 g, 10.7 mmol, 93.6% yield) as a brown oil. MS (ISP): m/z=566.1 [M+NH$_4$]$^+$ and 568.2 [M+2+NH$_4$]$^+$.

Synthesis of Intermediates A13

A13a: (R)—N-(2-(5-Bromo-2-fluorophenyl)-1-(cyanomethylthio)propan-2-yl)-2,2,2-trifluoroacetamide

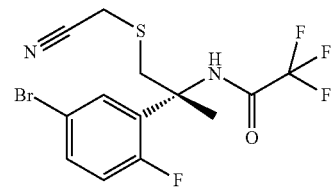 [SMILES: C[C@@](CSCC#N)(NC(=O)C(F)(F)F)c1cc(Br)ccc1F]

A mixture of (R)—N-(2-(5-bromo-2-fluorophenyl)-1-(cyanomethylthio)propan-2-yl)-N-(2,4-dimethoxybenzyl)-2,2,2-trifluoroacetamide (5.9 g, 10.7 mmol, Eq: 1.00) and trifluoroacetic acid (73.5 g, 49.6 ml, 644 mmol, Eq: 60) was stirred at 23° C. for 16 hours resulting in a dark red solution. Poured into sat. NaHCO$_3$-sol. and extracted twice with ethyl acetate. The combined organic layers were dried over Na$_2$SO$_4$, filtered and evaporated. The residue was purified by silica gel column chromatography 0 to 50% ethyl acetate in heptane to give the (R)—N-(2-(5-bromo-2-fluorophenyl)-1-(cyanomethylthio)propan-2-yl)-2,2,2-trifluoroacetamide Synthesis of Intermediates A14

A14a: (R)-2-(2-Amino-2-(5-bromo-2-fluorophenyl)propylthio)acetonitrile

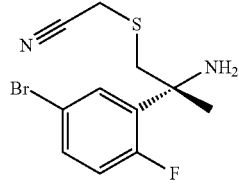 [SMILES: C[C@](N)(CSCC#N)c1cc(Br)ccc1F]

To a solution of (R)—N-(2-(5-bromo-2-fluorophenyl)-1-(cyanomethylthio)propan-2-yl)-2,2,2-trifluoroacetamide (3 g, 6.76 mmol, Eq: 1.00) in ethanol (30 ml) was added sodium borohydride (1.02 g, 27.1 mmol, Eq: 4.0) and the mixture was stirred at 23° C. for 16 hours. Poured into icecold sat. NH$_4$Cl-sol., stirred for 10 min and extracted twice with ethyl acetate. The combined organic layers were dried over Na$_2$SO$_4$, filtered and evaporated. The residue was purified by silica gel column chromatography with 0 to 50% ethyl acetate in heptane to give the (R)-2-(2-amino-2-(5-bromo-2-fluorophenyl)propylthio)acetonitrile (1.1 g, 3.63 mmol, 53.6% yield) as a light yellow oil. MS (ISP): m/z=303.0 [M+H]$^+$ and 304.9 [M+2H]$^+$.

Synthesis of Intermediates A15

A15a: (R)-5-(5-Bromo-2-fluorophenyl)-5-methyl-5,6-dihydro-2H-1,4-thiazin-3-amine

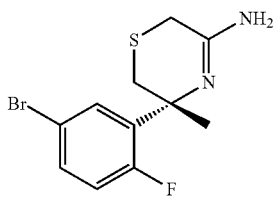 [SMILES: C[C@@]1(c2cc(Br)ccc2F)CSCC(N)=N1]

To a solution of (R)-2-(2-amino-2-(5-bromo-2-fluorophenyl)propylthio)acetonitrile (1.08 g, 3.56 mmol, Eq: 1.00) in toluene (20 ml) was dropwise added at 23° C. trimethylaluminum (2 M in toluene) (1.96 ml, 3.92 mmol, Eq: 1.1). The reaction mixture was stirred at 60° C. for 2 hours. The reaction mixture was carefully quenched by addition of water at 0° C., then extracted twice with 1 M Na$_2$CO$_3$-sol. and ethyl acetate. The combined organic layers were dried over Na$_2$SO$_4$, filtered and evaporated to give 1.5 g of a brown oil (139%). The residue was purified by silica gel column chromatography with dichloromethane+dichloromethane/methanol/ammonium hydroxide 110:10:1 to give the (R)-5-(5-bromo-2-fluorophenyl)-5-methyl-5,6-dihydro-2H-1,4-thiazin-3-amine (720 mg, 2.37 mmol, 66.7% yield) as a light brown gum. MS (ISP): m/z=303.0 [M+H]$^+$ and 305.0 [M+2+H]$^+$.

Synthesis of Intermediates A16

A16a: (R)-Ethyl 2-(2-(5-bromo-2-fluorophenyl)-2-(2,4-dimethoxybenzylamino) propylthio)acetate

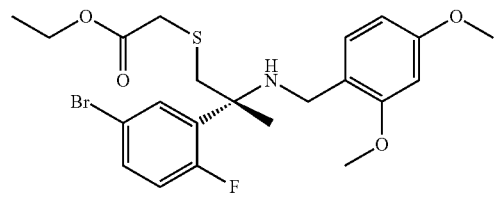 [SMILES: CCOC(=O)CSC[C@](C)(NCc1ccc(OC)cc1OC)c1cc(Br)ccc1F]

To a solution of (R)-4-(5-bromo-2-fluoro-phenyl)-3-(2,4-dimethoxy-benzyl)-4-methyl-[1,2,3]oxathiazolidine 2,2-dioxide (10 g, 21.7 mmol, Eq: 1.00) and ethyl thioglycolate (3.92 g, 3.57 ml, 32.6 mmol, Eq: 1.5) in DMF (134 ml) was added at 23° C. 1,1,3,3-tetramethylguanidine (3.75 g, 4.09 ml, 32.6 mmol, Eq: 1.5). The reaction mixture was stirred at 23° C. for 16 hours. The solution was evaporated at HV. The resulting residue was stirred vigorously overnight between 100 ml of dichloromethane and 20% (v/v) sulfuric acid solution (100 ml). Sat. NaHCO$_3$-solution was slowly added (pH=8), then extracted with dichloromethane twice. The combined organic layers were dried over Na$_2$SO$_4$, filtered and evaporated to give the crude product (14.4 g, 132%). The residue was chromatographed on 70 g silica gel with 0-50% ethyl acetate in heptane to give the (R)-ethyl 2-(2-(5-bromo-2-fluorophenyl)-2-(2,4-dimethoxybenzylamino)propylthio)acetate (10.9 g, 21.8 mmol, 100% yield) as a light yellow oil. MS (ISP): m/z=500.2 [M+H]$^+$ and 502.2 [M+2H]$^+$.

A16b: (R)-Ethyl 2-(2-(5-bromo-2-fluorophenyl)-2-(2,4-dimethoxybenzylamino)propylthio)-2-methylpropanoate

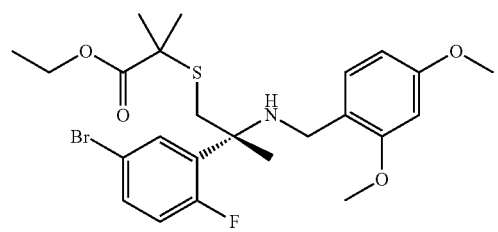 [SMILES: CCOC(=O)C(C)(C)SC[C@](C)(NCc1ccc(OC)cc1OC)c1cc(Br)ccc1F]

a) Ethyl 2-(acetylthio)-2-methylpropanoate: To a solution of ethyl 2-bromo-2-methylpropanoate (5 g, 3.81 ml, 25.6 mmol, Eq: 1.00) in acetone (150 ml) was added potassium thioacetate (3.22 g, 28.2 mmol, Eq: 1.10) at 23° C. The mixture was stirred for 2.5 hours at 60° C. Removing the solvent in vacuum, redissolved the orange solid in dichloromethane, washed with water, dried the organic layers over Na$_2$SO$_4$ and filtered off. Removal of solvent in vacuum left the ethyl 2-(acetylthio)-2-methylpropanoate (5.01 g, 25.0 mmol, 97.6% yield) as a yellow oil. The crude product was used in the next step without further purification.

b) Ethyl 2-mercapto-2-methylpropanoate: To a solution of ethyl 2-(acetylthio)-2-methylpropanoate (3.02 g, 15.9 mmol, Eq: 1.00) in methanol (150 ml) was added sodium methoxide (858 mg, 15.9 mmol, Eq: 1.00) at 23° C. The mixture was stirred for 4 hours at 23° C. Removed the solvent in vacuum, redissolved in dichloromethane, washed with water, dried over Na₂SO₄ and filtered off. Removal of solvent in vacuum left the resulting product as a mixture of ethyl 2-mercapto-2-methylpropanoate and the corresponding disulfide as a light brown oil (1.77 g) which was directly used without further purification.

c) To a solution of (R)-4-(5-bromo-2-fluoro-phenyl)-3-(2,4-dimethoxy-benzyl)-4-methyl-[1,2,3]oxathiazolidine 2,2-dioxide (2 g, 4.34 mmol, Eq: 1.00) and ethyl 2-mercapto-2-methylpropanoate (966 mg, 966 µl, 6.52 mmol, Eq: 1.5) in DMF (20 ml) was added at 23° C. 1,1,3,3-tetramethylguanidine (751 mg, 819 µl, 6.52 mmol, Eq: 1.5) and tri-n-butylphosphine (1.32 g, 1.61 ml, 6.52 mmol, Eq: 1.5) and the reaction mixture was stirred at 23° C. for 16 hours. The solution was evaporated at HV. The resulting residue was stirred vigorously overnight between 50 ml of dichloromethane and 20% (v/v) sulfuric acid solution (50 ml). Sat. NaHCO₃-sol. and 1 M Na₂CO₃-sol. was slowly added (pH=9), then extracted with dichloromethane twice. The combined organic layers were dried over Na₂SO₄, filtered and evaporated to give a yellow oil (3.51 g). The residue was chromatographed on 70 g silica gel with 0-50% ethyl acetate in heptane to give (R)-ethyl 2-(2-(5-bromo-2-fluorophenyl)-2-(2,4-dimethoxybenzylamino)propylthio)-2-methylpropanoate (2.3 g, 4.35 mmol, 100% yield) as a colorless oil. MS (ISP): m/z=528.2 [M+H]⁺ and 530.2 [M+2+H]⁺.

A16c: (R)-Ethyl 1-(2-(5-bromo-2-fluorophenyl)-2-(2,4-dimethoxybenzylamino) propylthio)cyclobutanecarboxylate

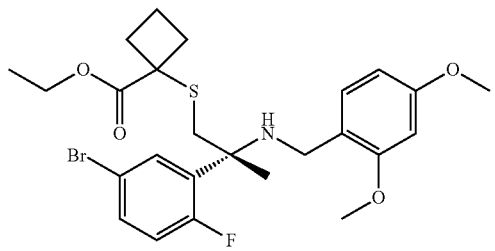 [SMILES: CCOC(=O)C1(SC[C@](C)(NCc2ccc(OC)cc2OC)c2cc(Br)ccc2F)CCC1]

a) Ethyl 1-(acetylthio)cyclobutanecarboxylate: To a solution of commercially available ethyl 1-bromocyclobutanecarboxylate (5 g, 24.1 mmol, Eq: 1.00) in acetone (48.3 ml) was added at 23° C. potassium thioacetate (3.03 g, 26.6 mmol, Eq: 1.1) and the reaction mixture was stirred at reflux for another 30 hours. The reaction mixture was concentrated in vacuum, the residue was extracted with diethyl ether and water. The organic layer was separated, dried over Na₂SO₄, filtered and evaporated. The residue was chromatographed twice on 70 g silica gel with 0-10% ethyl acetate in heptane to give ethyl 1-(acetylthio)cyclobutanecarboxylate (1.4 g, 6.3 mmol, 26.1% yield) as a brown liquid.

b) Ethyl 1-mercaptocyclobutanecarboxylate: To a solution of ethyl 1-(acetylthio)cyclobutanecarboxylate (1.4 g, 6.92 mmol, Eq: 1.00) in methanol (70 ml) was added sodium methoxide (374 mg, 6.92 mmol, Eq: 1.00) at 23° C. The mixture was stirred for 16 hours at 23° C. Diluted with water and sat. NaCl-sol., extracted with dichloromethane, dried the organic layer over Na₂SO₄ and filtered off. Removal of solvent in vacuum left a brown oil. The crude product was used in the next step without further purification.

c) To a solution of (R)-4-(5-bromo-2-fluoro-phenyl)-3-(2,4-dimethoxy-benzyl)-4-methyl-[1,2,3]oxathiazolidine 2,2-dioxide (2 g, 4.34 mmol, Eq: 1.00) and ethyl 1-mercaptocyclobutanecarboxylate (1.04 g, 6.52 mmol, Eq: 1.5) in DMF (21.7 ml) was added at 23° C. 1,1,3,3-tetramethylguanidine (751 mg, 819 µl, 6.52 mmol, Eq: 1.5) and tri-n-butylphosphine (1.32 g, 1.61 ml, 6.52 mmol, Eq: 1.5) and the reaction mixture was stirred at 23° C. for 20 hours. The solution was evaporated at HV. The resulting residue was stirred vigorously overnight between 40 ml of dichloromethane and 20% (v/v) sulfuric acid solution (40 ml). Sat. NaHCO₃-sol. and 1 M Na₂CO₃-sol. was slowly added (pH=10), then extracted with dichloromethane twice. The combined organic layers were dried over Na₂SO₄, filtered and evaporated to give a brown oil (3.32 g). The residue was chromatographed on 70 g silica gel with 0-50% ethyl acetate in heptane to give (R)-ethyl 1-(2-(5-bromo-2-fluorophenyl)-2-(2,4-dimethoxybenzylamino)propylthio)cyclobutanecarboxylate (1.98 g, 3.66 mmol, 84.3% yield) as a light yellow oil. MS (ISP): m/z=540.2 [M+H]⁺ and 542.3 [M+2+H]⁺.

Synthesis of Intermediates A17

A17a: (R)-2-(2-(5-Bromo-2-fluorophenyl)-2-(2,4-dimethoxybenzylamino)propylthio)acetic acid

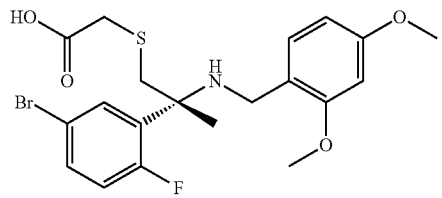 [SMILES: COc1ccc(CN[C@@](C)(CSCC(=O)O)c2cc(Br)ccc2F)c(OC)c1]

To a solution of (R)-ethyl 2-(2-(5-bromo-2-fluorophenyl)-2-(2,4-dimethoxybenzylamino)propylthio)acetate (3 g, 5.99 mmol, Eq: 1.00) in tetrahydrofuran (20 ml), methanol (10 ml), water (5 ml) was added at 23° C. lithium hydroxide (287 mg, 12.0 mmol, Eq: 2.0). The colourless reaction solution was stirred at 23° C. for 2 hours. The reaction mixture was neutralized with 1 N HCl (12.0 ml, 12.0 mmol, Eq: 2.0) (pH=5-6) and evaporated. The residue was triturated with dichloromethane/methanol 9:1 and solid Na₂SO₄ was added. The solid was filtered off and the filtrate was evaporated to dryness to give the crude (R)-2-(2-(5-bromo-2-fluorophenyl)-2-(2,4-dimethoxybenzylamino)propylthio)acetic acid (3.2 g, 6.1 mmol, 102% yield) as a white foam which was used without further purification. MS (ISN): m/z=470.6 [M−H]⁻ and 472.5 [M+2−H]⁻.

A17b: (R)-2-(2-(5-Bromo-2-fluorophenyl)-2-(2,4-dimethoxybenzylamino)propylthio)-2-methylpropanoic acid

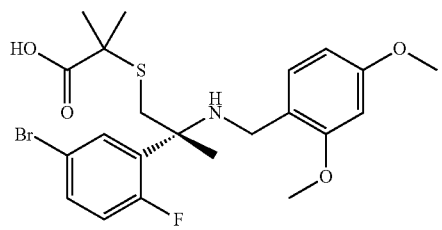 [SMILES: COc1ccc(CN[C@@](C)(CSC(C)(C)C(=O)O)c2cc(Br)ccc2F)c(OC)c1]

To a solution of (R)-ethyl 2-(2-(5-bromo-2-fluorophenyl)-2-(2,4-dimethoxybenzylamino) propylthio)-2-methylpropanoate (3 g, 5.68 mmol, Eq: 1.00) in ethanol (35.7 ml) was added 3 N NaOH (3.78 ml, 11.4 mmol, Eq: 2.0). The reaction mixture was stirred at 70° C. for 2 hours. 1 N HCl (11.4 ml, 11.4 mmol, Eq: 2.0) was added to the reaction mixture at 23° C. (pH=5-6) and evaporated. The residue was triturated with dichloromethane/methanol 9:1, solid Na$_2$SO$_4$ was added. The mixture was filtered off. The filtrate was evaporated to dryness to give the crude (R)-2-(2-(5-bromo-2-fluorophenyl)-2-(2,4-dimethoxybenzylamino)propylthio)-2-methylpropanoic acid (2.6 g, 5.2 mmol, 91.5% yield) as an off-white foam which was used without further purification. MS (ISP): m/z=500.0 [M+H]$^+$ and 502.3 [M+2+H]$^+$.

A17c: (R)-1-(2-(5-Bromo-2-fluorophenyl)-2-(2,4-dimethoxybenzylamino)propylthio)cyclobutanecarboxylic acid

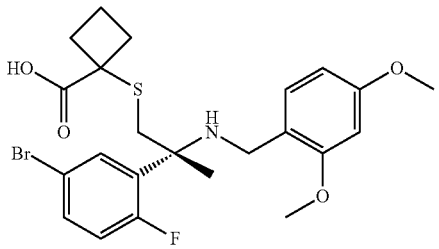 [SMILES: COc1ccc(CN[C@@](C)(CSC2(C(=O)O)CCC2)c2cc(Br)ccc2F)c(OC)c1]

To a solution of (R)-ethyl 1-(2-(5-bromo-2-fluorophenyl)-2-(2,4-dimethoxybenzylamino)propylthio)cyclobutanecarboxylate (2 g, 3.7 mmol, Eq: 1.00) in ethanol (50 ml) was added 3 N NaOH (2.47 ml, 7.4 mmol, Eq: 2.0). The reaction solution was stirred at 70° C. for 2 hours. 1 N HCl (7.4 ml, 7.4 mmol, Eq: 2.0) was added to the reaction mixture at 23° C. (pH=5-6). After evaporation the residue was triturated with dichloromethane/methanol 9:1 and solid Na$_2$SO$_4$ was added. The solid was filtered off and the filtrate was evaporated to dryness to give the crude (R)-1-(2-(5-bromo-2-fluorophenyl)-2-(2,4-dimethoxybenzylamino)propylthio)cyclobutanecarboxylic acid (1.8 g, 3.51 mmol, 94.9% yield) as a white foam, which was used without further purification. MS (ISP): m/z=512.4 [M+H]$^+$ and 514.4 [M+2+H]$^+$.

Synthesis of Intermediates A18

A18a: (R)-5-(5-Bromo-2-fluorophenyl)-4-(2,4-dimethoxybenzyl)-5-methylthiomorpholin-3-one

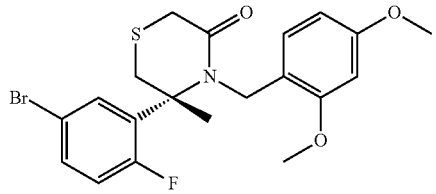 [SMILES: COc1ccc(CN2C(=O)CSC[C@@]2(C)c2cc(Br)ccc2F)c(OC)c1]

To a solution of (R)-2-(2-(5-bromo-2-fluorophenyl)-2-(2,4-dimethoxybenzylamino) propylthio)acetic acid (3.3 g, 6.99 mmol, Eq: 1.00) and N,N-diisopropylethylamine (2.71 g, 3.66 ml, 21.0 mmol, Eq: 3.0) in ethyl acetate (194 ml) was added at 23° C. 1-propanephosphonic acid cyclic anhydride (50% solution in ethyl acetate) (6.67 g, 6.23 ml, 10.5 mmol, Eq: 1.5) and the colourless reaction solution was stirred at 23° C. for 2 hours. The reaction mixture was washed with sat NaHCO$_3$-sol., water and brine. The organic layer was dried over Na$_2$SO$_4$, filtered and evaporated to give the nearly pure (R)-5-(5-bromo-2-fluorophenyl)-4-(2,4-dimethoxybenzyl)-5-methylthiomorpholin-3-one (2.95 g, 6.49 mmol, 92.9% yield) as a colourless oil, which crystallized in the fridge and was used without further purification. MS (ISP): m/z=454.0 [M+H]$^+$ and 456.1 [M+2+H]$^+$.

A18b: (R)-5-(5-Bromo-2-fluorophenyl)-4-(2,4-dimethoxybenzyl)-2,2,5-trimethylthiomorpholin-3-one

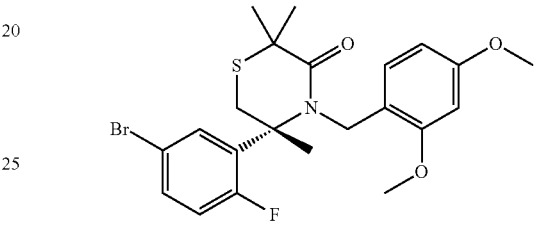

To a solution of (R)-2-(2-(5-bromo-2-fluorophenyl)-2-(2,4-dimethoxybenzylamino) propylthio)-2-methylpropanoic acid (2.6 g, 5.2 mmol, Eq: 1.00) and diisopropylethylamine (2.01 g, 2.72 ml, 15.6 mmol, Eq: 3.0) in ethyl acetate (104 ml) was added at 23° C. 1-propanephosphonic acid cyclic anhydride (50% solution in ethyl acetate) (4.96 g, 4.63 ml, 7.79 mmol, Eq: 1.5). The colourless reaction solution was stirred at 23° C. for 2 hours. The reaction mixture was washed with sat NaHCO$_3$-sol., water and brine. The organic layer was dried over Na$_2$SO$_4$, filtered and evaporated to give the crude and nearly pure (R)-5-(5-bromo-2-fluorophenyl)-4-(2,4-dimethoxybenzyl)-2,2,5-trimethylthiomorpholin-3-one (2.45 g, 5.08 mmol, 97.7% yield) as a colourless oil which crystallized in the fridge. MS (ISP): m/z=482.0 [M+H]$^+$ and 484.3 [M+2+H]$^+$.

A18c: (R)-7-(5-Bromo-2-fluorophenyl)-8-(2,4-dimethoxybenzyl)-7-methyl-5-thia-8-azaspiro[3.5]nonan-9-one

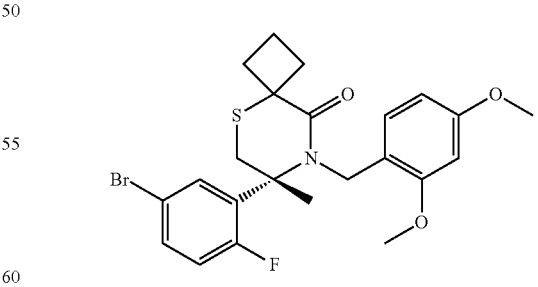

To a solution of (R)-1-(2-(5-bromo-2-fluorophenyl)-2-(2,4-dimethoxybenzylamino) propylthio)cyclobutanecarboxylic acid (1.8 g, 3.51 mmol, Eq: 1.00) and diisopropylethylamine (1.36 g, 1.84 ml, 10.5 mmol, Eq: 3.0) in ethyl acetate (70.3 ml) was added at 23° C. 1-propanephosphonic acid cyclic anhydride (50% solution in ethyl acetate) (3.35 g, 3.08 ml, 5.27 mmol, Eq: 1.5). The colourless reaction solution was stirred at 23° C. for 16 hours. The reaction mixture was washed with sat. NaHCO$_3$-sol., water and brine. The organic layer was dried over Na$_2$SO$_4$, filtered and evaporated to give the crude and pure (R)-7-(5-bromo-2-fluorophenyl)-8-(2,4-dimethoxybenzyl)-7-methyl-5-thia-8-azaspiro[3.5]nonan-9-one (1.75 g, 3.54 mmol, 101% yield) as a white foam. MS (ISP): m/z=494.0 [M+H]$^+$ and 496.4 [M+2+H]$^+$.

Synthesis of Intermediates A19

A19a: (R)-5-(5-Bromo-2-fluoro-phenyl)-4-(2,4-dimethoxy-benzyl)-5-methyl-1,1-dioxo-1λ6-thiomorpholin-3-one

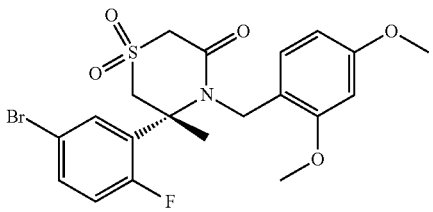 [SMILES: COc1ccc(CN2C(=O)CS(=O)(=O)C[C@@]2(C)c2cc(Br)ccc2F)c(OC)c1]

To a solution of (R)-5-(5-bromo-2-fluorophenyl)-4-(2,4-dimethoxybenzyl)-5-methylthiomorpholin-3-one (2.95 g, 6.49 mmol, Eq: 1.00) in methanol (100 ml) was added at 23° C. Oxone® (7.98 g, 13.0 mmol, Eq: 2.00). The reaction mixture was stirred at 23° C. for 16 hours. The reaction mixture was carefully quenched by addition of water at 0° C., then 10 ml of a diluted NaHSO$_3$-solution, sat. NaHCO$_3$-solution and ethyl acetate were added. Vigorous stirring was continued for 10 min. The organic layer was separated and washed with water, then dried over Na$_2$SO$_4$, filtered and evaporated to give a yellow oil which was chromatographed on 20 g silica gel with 0-50% ethyl acetate in heptane to give (R)-5-(5-bromo-2-fluoro-phenyl)-4-(2,4-dimethoxy-benzyl)-5-methyl-1,1-dioxo-1λ6-thiomorpholin-3-one (3 g, 6.17 mmol, 95.0% yield) as a white foam. MS (ISP): m/z=486.2 [M+H]$^+$ and 488.1 [M+2+H]$^+$.

A19b: (R)-5-(5-Bromo-2-fluoro-phenyl)-4-(2,4-dimethoxy-benzyl)-2,2,5-trimethyl-1,1-dioxo-1λ6-thiomorpholin-3-one

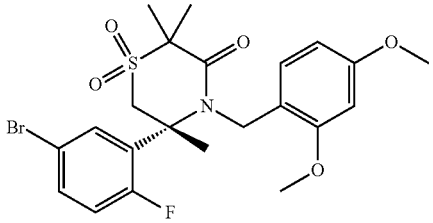 [SMILES: COc1ccc(CN2C(=O)C(C)(C)S(=O)(=O)C[C@@]2(C)c2cc(Br)ccc2F)c(OC)c1]

To a solution of (R)-5-(5-bromo-2-fluorophenyl)-4-(2,4-dimethoxybenzyl)-2,2,5-trimethylthiomorpholin-3-one (2.45 g, 5.08 mmol, Eq: 1.00) in methanol (60 ml) was added at 23° C. Oxone® (6.24 g, 10.2 mmol, Eq: 2.00). The reaction mixture was stirred at 23° C. for 16 hours. The reaction mixture was carefully quenched by addition of water at 0° C. 10 ml of a diluted NaHSO$_3$ solution, sat. NaHCO$_3$ solution and ethyl acetate were added. Vigorous stirring was continued for 10 min. The organic layer was separated and washed with water, then dried over Na$_2$SO$_4$, filtered and evaporated to give the crude and nearly pure (R)-5-(5-bromo-2-fluoro-phenyl)-4-(2,4-dimethoxy-benzyl)-2,2,5-trimethyl-1,1-dioxo-1λ6-thiomorpholin-3-one (2.47 g, 4.80 mmol, 94.5% yield) as orange foam. MS (ISP): m/z=514.2 [M+H]$^+$ and 516.3 [M+2+H]$^+$.

A19c: (R)-2,2-Diallyl-5-(5-bromo-2-fluoro-phenyl)-4-(2,4-dimethoxy-benzyl)-5-methyl-1,1-dioxo-1λ6-thiomorpholin-3-one

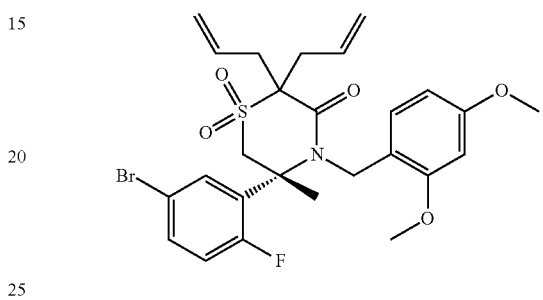

To a solution of (R)-5-(5-bromo-2-fluoro-phenyl)-4-(2,4-dimethoxy-benzyl)-5-methyl-1,1-dioxo-1λ6-thiomorpholin-3-one (1 g, 2.06 mmol, Eq: 1.00) in acetone (8 ml) was added allyl bromide (547 mg, 391 µl, 4.52 mmol, Eq: 2.2), then potassium carbonate (853 mg, 6.17 mmol, Eq: 3.0). The reaction suspension was stirred in a sealed tube for 4 days. Extracted with water and ethyl acetate, the organic layer was separated, dried over Na$_2$SO$_4$, filtered and evaporated to dryness. The residue was chromatographed on 20 g silica gel with 0% to 50% ethyl acetate in heptane to give (R)-2,2-diallyl-5-(5-bromo-2-fluoro-phenyl)-4-(2,4-dimethoxy-benzyl)-5-methyl-1,1-dioxo-1λ6-thiomorpholin-3-one (620 mg, 1.09 mmol, 53.2% yield) as a white foam. MS (ISP): m/z=566.2 [M+H]$^+$ and 568.1 [M+2+H]$^+$.

A19d: (R)-8-(5-Bromo-2-fluoro-phenyl)-9-(2,4-dimethoxy-benzyl)-8-methyl-6,6-dioxo-6λ6-thia-9-aza-spiro[4.5]dec-2-en-10-one

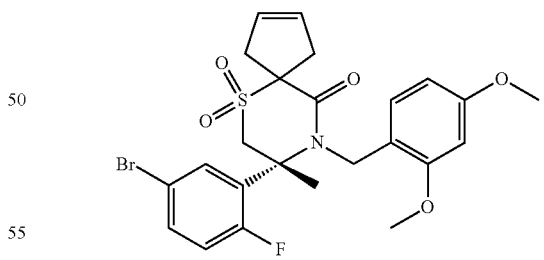

To a solution of (R)-2,2-diallyl-5-(5-bromo-2-fluoro-phenyl)-4-(2,4-dimethoxy-benzyl)-5-methyl-1,1-dioxo-1λ6-thiomorpholin-3-one (610 mg, 1.08 mmol, Eq: 1.00) in dichloromethane (20.3 ml) was added under argon [1,3-bis-(2,4,6-trimethylphenyl)-2-imidazolidinylidene]dichloro (phenylmethylene)(tricyclohexylphosphine)ruthenium (Grubbs II catalyst) (45.7 mg, 53.8 µmol, Eq: 0.05). The reaction mixture was stirred at reflux for 4 hours. Evaporation and chromatography on 20 g silica gel with 0% to 50% ethyl acetate in heptane gave the (R)-8-(5-bromo-2-fluoro-phenyl)-9-(2,4-dimethoxy-benzyl)-8-methyl-6,6-dioxo-6λ6-thia-9-aza-spiro[4.5]dec-2-en-10-one (460 mg, 854 µmol, 79.3% yield) as a white foam. MS (ISP): m/z=538.2 [M+H]+ and 540.2 [M+2+H]+.

A19e: (R)-7-(5-Bromo-2-fluoro-phenyl)-8-(2,4-dimethoxy-benzyl)-7-methyl-5,5-dioxo-5λ6-thia-8-aza-spiro[3.5]nonan-9-one

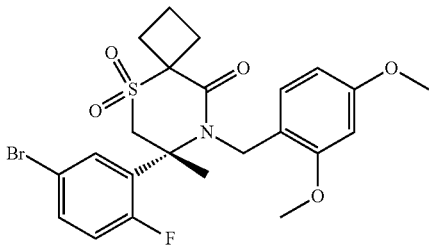 [SMILES: COc1ccc(CN2C(=O)C3(CCC3)S(=O)(=O)C[C@@]2(C)c2cc(Br)ccc2F)c(OC)c1]

To a solution of (R)-7-(5-bromo-2-fluorophenyl)-8-(2,4-dimethoxybenzyl)-7-methyl-5-thia-8-azaspiro[3.5]nonan-9-one (1.7 g, 3.44 mmol, Eq: 1.00) in methanol (50 ml) was added at 23° C. Oxone® (4.23 g, 6.88 mmol, Eq: 2.00). The reaction mixture was stirred at 23° C. for 24 hours. The reaction mixture was carefully quenched by addition of water at 0° C., 10 ml of a diluted NaHSO3 solution, sat. NaHCO3 solution and ethyl acetate were added. Vigorous stirring was continued for 10 min. The organic layer was separated and washed with water, then dried over Na2SO4, filtered and evaporated to give (R)-7-(5-bromo-2-fluoro-phenyl)-8-(2,4-dimethoxy-benzyl)-7-methyl-5,5-dioxo-5λ6-thia-8-aza-spiro[3.5]nonan-9-one (1.9 g, 3.25 mmol, 94.5% yield) as an off-white foam. MS (ISP): m/z=526.4 [M+H]+ and 528.3 [M+2+H]+.

Synthesis of Intermediates A20

A20a: (R)-5-(5-Bromo-2-fluoro-phenyl)-5-methyl-1,1-dioxo-1λ6-thiomorpholin-3-one

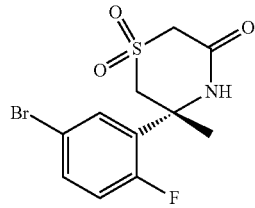 [SMILES: C[C@@]1(c2cc(Br)ccc2F)CS(=O)(=O)CC(=O)N1]

A mixture of (R)-5-(5-bromo-2-fluoro-phenyl)-4-(2,4-dimethoxy-benzyl)-5-methyl-1,1-dioxo-1λ6-thiomorpholin-3-one (251 mg, 516 µmol, Eq: 1.00) and trifluoroacetic acid (5.88 g, 3.98 ml, 51.6 mmol, Eq: 100) was stirred at 23° C. for 16 hours. Poured into 1 M Na2CO3-sol. and extracted twice with ethyl acetate. The combined organic layers were dried over Na2SO4, filtered and evaporated. The residue was chromatographed on 5 g silica gel with dichloromethane/ethyl acetate 9:1 to give (R)-5-(5-bromo-2-fluoro-phenyl)-5-methyl-1,1-dioxo-1λ6-thiomorpholin-3-one (116 mg, 345 µmol, 66.9% yield) as a white solid. MS (ISN): m/z=334.0 [M−H]− and 336.0 [M+2−H]−.

A20b: (R)-5-(5-Bromo-2-fluoro-phenyl)-2,2,5-trimethyl-1,1-dioxo-1λ6-thiomorpholin-3-one

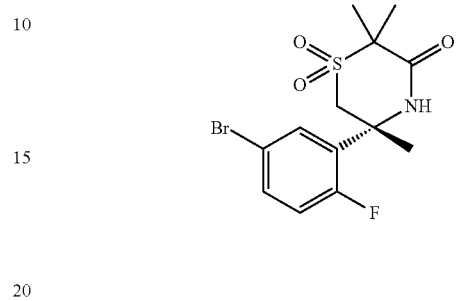

A mixture of (R)-5-(5-bromo-2-fluoro-phenyl)-5-methyl-1,1-dioxo-1λ6-thio morpholin-3-one (2.1 g, 4.08 mmol, Eq: 1.00) and trifluoroacetic acid (46.5 g, 31.5 ml, 408 mmol, Eq: 100) was stirred at 23° C. After 1 hour trifluoromethanesulfonic acid (1.23 g, 725 µl, 8.16 mmol, Eq: 2.0) was added and stirring continued for 2 hours. Poured into 1 M Na2CO3-sol. and extracted twice with ethyl acetate. The combined organic layers were dried over Na2SO4, filtered and evaporated. The residue was chromatographed on 70 g silica gel with heptane/ethyl acetate 1:1 to give (R)-5-(5-bromo-2-fluoro-phenyl)-2,2,5-trimethyl-1,1-dioxo-1λ6-thio morpholin-3-one (1.4 g, 3.84 mmol, 94.2% yield) as an off-white solid. MS (ISP): m/z=364.0 [M+H]+ and 366.3 [M+2+H]+.

A20c: (R)-8-(5-Bromo-2-fluoro-phenyl)-8-methyl-6,6-dioxo-6λ6-thia-9-aza-spiro[4.5]dec-2-en-10-one

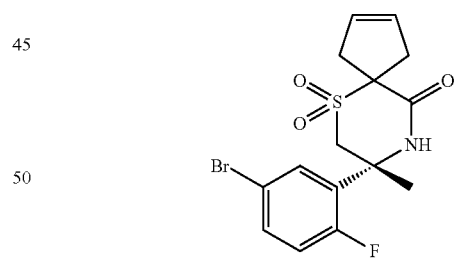

A mixture of (R)-8-(5-bromo-2-fluoro-phenyl)-9-(2,4-dimethoxy-benzyl)-8-methyl-6,6-dioxo-6λ6-thia-9-aza-spiro[4.5]dec-2-en-10-one (450 mg, 836 µmol, Eq: 1.00) and trifluoroacetic acid (9.53 g, 6.44 ml, 83.6 mmol, Eq: 100) was stirred at 23° C. After 1 hour trifluoromethanesulfonic acid (251 mg, 148 µl, 1.67 mmol, Eq: 2.0) was added and the dark red solution was stirred for 2 hours. Poured into 1 M Na2CO3-sol. and extracted twice with ethyl acetate. The combined organic layers were dried over Na2SO4, filtered and evaporated. The residue was chromatographed on 10 g silica gel with heptane/ethyl acetate 1:1 to give (R)-8-(5-bromo-2-fluoro-phenyl)-8-methyl-6,6-dioxo-6λ6-thia-9-aza-spiro

[4.5]dec-2-en-10-one (340 mg, 788 µmol, 94.3% yield) as a white solid. MS (ISP): m/z=388.1 [M+H]⁺ and 390.2 [M+2+H]⁺.

A20d: (R)-7-(5-Bromo-2-fluoro-phenyl)-7-methyl-5,5-dioxo-5λ6-thia-8-aza-Spiro[3.5]nonan-9-one

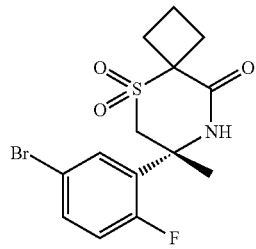

A mixture of RO6883781-000-001 (1.9 g, 3.25 mmol, Eq: 1.00) and trifluoroacetic acid (29.6 g, 20.0 ml, 260 mmol, Eq: 80) was stirred at 23° C. After 1 hour trifluoromethanesulfonic acid (975 mg, 577 µl, 6.5 mmol, Eq: 2.0) was added and stirring of the dark red solution was continued for 2 hours. Poured into 1 M Na₂CO₃ solution and extracted twice with ethyl acetate. The combined organic layers were dried over Na₂SO₄, filtered and evaporated. The residue was chromatographed on 20 g silica gel with heptane/ethyl acetate 1:1 to give the (R)-7-(5-bromo-2-fluoro-phenyl)-7-methyl-5,5-dioxo-5λ6-thia-8-aza-spiro[3.5]nonan-9-one (1.1 g, 2.92 mmol, 90.0% yield) as a light red solid. MS (ISP): m/z=376.0 [M+H]⁺ and 378.4 [M+2+H]⁺.

Synthesis of Intermediates A21

A21a: (R)-5-(5-Bromo-2-fluoro-phenyl)-5-methyl-1,1-dioxo-1λ6-thiomorpholin-3-thione

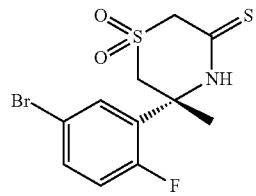

To a solution of (R)-5-(5-bromo-2-fluoro-phenyl)-5-methyl-1,1-dioxo-1λ6-thio morpholin-3-one (3.11 g, 9.25 mmol, Eq: 1.00) in dioxane (72.3 ml) was added Lawesson's reagent (2.99 g, 7.4 mmol, Eq: 0.8) at 23° C. The mixture was stirred for 2 hours at 80° C. Diluted with sat. NaHCO₃-sol., extracted with ethyl acetate, washed with brine, dried over Na₂SO₄ and filtered off. Removal of solvent in vacuum left a yellow oil (5.8 g), which was purified by flash chromatography on 50 g silica gel with 0-50% ethyl acetate in heptane to give the (R)-5-(5-bromo-2-fluoro-phenyl)-5-methyl-1,1-dioxo-1λ6-thio morpholin-3-thione (2.7 g, 7.67 mmol, 82.9% yield) as a light yellow foam. MS (ISN): m/z=350.1 [M−H]⁻ and 352.2 [M+2−H]⁻.

A21b: (R)-5-(5-Bromo-2-fluoro-phenyl)-2,2,5-trimethyl-1,1-dioxo-1λ6-thiomorpholin-3-thione

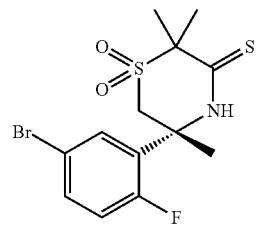 [SMILES: CC1(C)C(=O)N[C@](C)(c2cc(Br)ccc2F)CS1(=O)=O]

To a solution of (R)-5-(5-bromo-2-fluoro-phenyl)-2,2,5-trimethyl-1,1-dioxo-1λ6-thiomorpholin-3-one (1.4 g, 3.84 mmol, Eq: 1.00) in dioxane (29.5 ml) was added Lawesson's reagent (3.10 g, 7.68 mmol, Eq: 2.00). The reaction mixture was stirred at 80° C. for 10 hours. The reaction mixture was poured into sat. NaHCO₃-solution and extracted twice with ethyl acetate. The organic layers were washed with brine, dried over Na₂SO₄, filtered and evaporated to give a light yellow oil. The residue was chromatographed on 20 g silica gel with ethyl acetate in heptane to give (R)-5-(5-bromo-2-fluoro-phenyl)-2,2,5-trimethyl-1,1-dioxo-1λ6-thiomorpholin-3-thione (1.3 g, 3.42 mmol, 88.9% yield) as a light yellow foam. MS (ISP): m/z=380.0 [M+H]⁺ and 382.3 [M+2+H]⁺.

A21c: (R)-8-(5-Bromo-2-fluoro-phenyl)-8-methyl-6,6-dioxo-6λ6-thia-9-aza-spiro[4.5]dec-2-en-10-thione

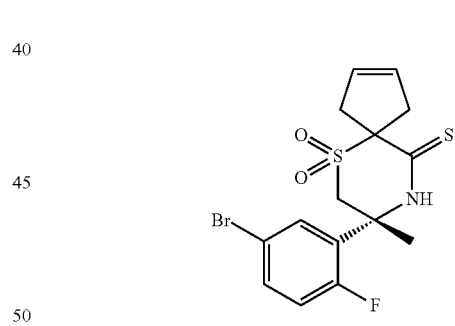

A mixture of (R)-8-(5-bromo-2-fluoro-phenyl)-8-methyl-6,6-dioxo-6λ6-thia-9-aza-spiro[4.5]dec-2-en-10-one (410 mg, 1.06 mmol, Eq: 1.00) and Lawesson's reagent (427 mg, 1.06 mmol, Eq: 1.00) in dioxane (10 ml) was stirred at 80° C. for 2 hours. More Lawesson's reagent (427 mg, 1.06 mmol, Eq: 1.00) was added and stirring continued at 85° C. for 16 hours. More Lawesson's reagent (427 mg, 1.06 mmol, Eq: 1.00) was added and stirring continued at 95° C. for 6 hours. The reaction mixture was poured into sat. NaHCO₃-solution and extracted twice with ethyl acetate. The organic layers were washed with brine, dried over Na₂SO₄, filtered and evaporated to give light yellow oil. The residue was chromatographed on 20 g silica gel with dichloromethane/heptane to give (R)-8-(5-bromo-2-fluoro-phenyl)-8-methyl-6,6-dioxo-6λ6-thia-9-aza-spiro[4.5]dec-2-en-10-thione (305 mg, 754 μmol, 71.4% yield) as a light yellow foam. MS (ISP): m/z=404.1 [M+H]⁺ and 406.2 [M+2+H]⁺.

A21d: (R)-7-(5-Bromo-2-fluoro-phenyl)-7-methyl-5,5-dioxo-5λ6-thia-8-aza-spiro[3.5]nonan-9-thione

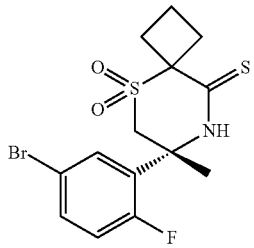 [SMILES: C[C@@]1(c2cc(Br)ccc2F)CS(=O)(=O)C2(CCC2)C(=S)N1]

To a solution of (R)-7-(5-bromo-2-fluoro-phenyl)-7-methyl-5,5-dioxo-5λ6-thia-8-aza-spiro[3.5]nonan-9-one (1.1 g, 2.92 mmol, Eq: 1.00) in dioxane (50 ml) was added Lawesson's reagent (1.18 g, 2.92 mmol, Eq: 1.00). The reaction mixture was stirred at 80° C. for 2 hours. More Lawesson's reagent (1.55 g, 3.84 mmol, Eq: 1.00) was added and stirring continued at 80° C. for 8 hours. The reaction mixture was poured into sat. NaHCO₃ solution and extracted twice with ethyl acetate. The organic layers were washed with brine, dried over Na₂SO₄, filtered and evaporated to give light yellow oil. The residue was chromatographed on 20 g silica gel with 0-50% ethyl acetate in heptane to give (R)-7-(5-bromo-2-fluoro-phenyl)-7-methyl-5,5-dioxo-5λ6-thia-8-aza-spiro[3.5]nonan-9-thione (1.05 g, 2.68 mmol, 91.5% yield) as a light yellow foam. MS (ISP): m/z=392.0 [M+H]⁺ and 394.3 [M+2+H]⁺.

Synthesis of Intermediates A22

A22a: (R)-5-(5-Bromo-2-fluoro-phenyl)-5-methyl-1,1-dioxo-1,2,5,6-tetrahydro-1λ6-[1,4]thiazin-3-ylamine

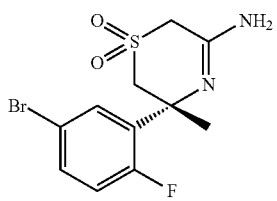 [SMILES: C[C@@]1(c2cc(Br)ccc2F)CS(=O)(=O)CC(N)=N1]

A mixture of (R)-5-(5-bromo-2-fluoro-phenyl)-5-methyl-1,1-dioxo-1λ6-thiomorpholin-3-thione (2.7 g, 7.67 mmol, Eq: 1.00) in ammonia (7 M in MeOH) (47.2 g, 60 ml, 420 mmol, Eq: 54.8) was stirred at 60° C. in a sealed tube for 5 hours. The yellow solution was evaporated, then chromatographed on 20 g silica gel with 0-80% ethyl acetate in heptane to give the (R)-5-(5-bromo-2-fluoro-phenyl)-5-methyl-1,1-dioxo-1,2,5,6-tetrahydro-1λ6-[1,4]thiazin-3-ylamine (1.78 g, 5.31 mmol, 69.3% yield) as a white foam. MS (ISP): m/z=335.0 [M+H]⁺ and 337.0 [M+2+H]⁺.

A22b: (R)-5-(2-Fluoro-phenyl)-5-methyl-1,1-dioxo-1,2,5,6-tetrahydro-1λ6-[1,4]thiazin-3-ylamine

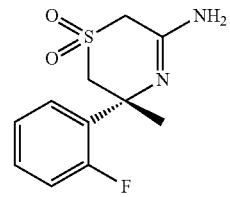 [SMILES: C[C@@]1(c2ccccc2F)CS(=O)(=O)CC(N)=N1]

To a solution of (R)-5-(5-bromo-2-fluoro-phenyl)-5-methyl-1,1-dioxo-1,2,5,6-tetrahydro-1λ6-[1,4]thiazin-3-ylamine (750 mg, 2.24 mmol, Eq: 1.00) in methanol (150 ml) and 7 M ammonia in methanol (959 μl, 6.71 mmol, Eq: 3) at room temperature added Pd/C (238 mg, 224 mmol, Eq: 0.1) and the mixture was hydrogenated at room temperature for 2 hours. Extracted with dichloromethane and some 25% ammonium hydroxide solution. Dried the organic layer over Na₂SO₄, filtered off and evaporated totally, dried in HV to give the (R)-5-(2-fluoro-phenyl)-5-methyl-1,1-dioxo-1,2,5,6-tetrahydro-1λ6-[1,4]thiazin-3-ylamine (497 mg, 1.94 mmol, 86.7% yield) as a white foam. MS (ISP): m/z=257.1 [M+H]⁺.

A22c: (R)-5-(5-Bromo-2-fluoro-phenyl)-2,2,5-trimethyl-1,1-dioxo-1,2,5,6-tetrahydro-1λ6-[1,4]thiazin-3-ylamine

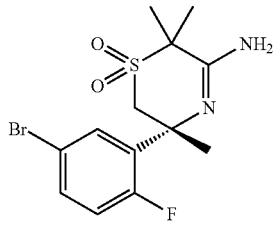 [SMILES: CC1(C)C(N)=N[C@](C)(c2cc(Br)ccc2F)CS1(=O)=O]

A mixture of (R)-5-(5-bromo-2-fluoro-phenyl)-2,2,5-trimethyl-1,1-dioxo-1λ6-thiomorpholin-3-thione (1.28 g, 3.37 mmol, Eq: 1.00) and ammonia (7 N in MeOH) (38.5 ml, 269 mmol, Eq: 80) was stirred in a sealed tube for 20 hours at 60° C. Extracted with ethyl acetate/sat. NaHCO₃-sol., dried the organic layer over Na₂SO₄, filtered and evaporated. The residue was chromatographed with ethyl acetate to give (R)-5-(5-bromo-2-fluoro-phenyl)-2,2,5-trimethyl-1,1-dioxo-1,2,5,6-tetrahydro-1λ6-[1,4]thiazin-3-ylamine (1 g, 2.75 mmol, 81.8% yield) as a white solid. MS (ISP): m/z=363.3 [M+H]⁺ and 365.3 [M+2+H]⁺.

A22d: (R)-5-(2-Fluoro-phenyl)-2,2,5-trimethyl-1,1-dioxo-1,2,5,6-tetrahydro-1λ6-[1,4]thiazin-3-ylamine

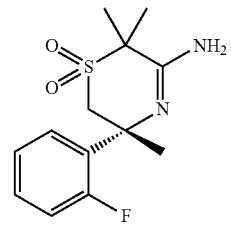 [SMILES: CC1(C)C(N)=N[C@](C)(c2ccccc2F)CS1(=O)=O]

To a solution of (R)-5-(5-bromo-2-fluoro-phenyl)-2,2,5-trimethyl-1,1-dioxo-1,2,5,6-tetrahydro-1λ6-[1,4]thiazin-3-ylamine (1 g, 2.75 mmol, Eq: 1.00) in methanol (80 ml) and ammonia (7 M in MeOH) (1.18 ml, 8.26 mmol, Eq: 3.0) was added at 23° C. under inert atmosphere Pd/C 10% (293 mg, 275 µmol, Eq: 0.1) and the suspension was set under hydrogen (balloon) and stirred at 23° C. for 2 hours. The catalyst was filtered off, washed three times with methanol and evaporated. The residue was extracted with dichloromethane/sat. NaHCO₃-sol. and the organic layer was dried over Na₂SO₄, filtered and evaporated to give the pure (R)-5-(2-fluoro-phenyl)-2,2,5-trimethyl-1,1-dioxo-1,2,5,6-tetrahydro-1λ6-[1,4]thiazin-3-ylamine (760 mg, 2.67 mmol, 97.1% yield) as a white solid. MS (ISP): m/z=285.4 [M+H]⁺.

A22e: (R)-8-(5-Bromo-2-fluoro-phenyl)-8-methyl-6,6-dioxo-6λ6-thia-9-aza-spiro[4.5]deca-2,9-dien-10-ylamine

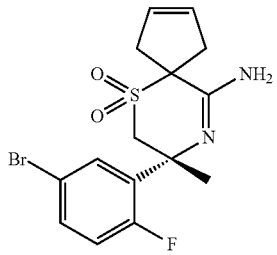 [SMILES: C[C@@]1(c2cc(Br)ccc2F)CS(=O)(=O)C2(CC=CC2)C(N)=N1]

A mixture of (R)-8-(5-bromo-2-fluoro-phenyl)-8-methyl-6,6-dioxo-6λ6-thia-9-aza-spiro[4.5]dec-2-en-10-thione (300 mg, 742 µmol, Eq: 1.00) and ammonia (7 N in MeOH) (7.87 g, 10 ml, 70.0 mmol, Eq: 94.3) was stirred in a sealed tube for 48 hours at 60° C. Extracted with ethyl acetate and sat. NaHCO₃-sol., dried the organic layer over Na₂SO₄, filtered and evaporated. The residue was chromatographed with ethyl acetate to give (R)-8-(5-bromo-2-fluoro-phenyl)-8-methyl-6,6-dioxo-6λ6-thia-9-aza-spiro[4.5]deca-2,9-dien-10-ylamine (249 mg, 643 µmol, 86.7% yield) as a white foam. MS (ISP): m/z=387.3 [M+H]⁺ and 389.3 [M+2+H]⁺.

A22f: (R)-8-(2-Fluoro-phenyl)-8-methyl-6,6-dioxo-6λ6-thia-9-aza-spiro[4.5]dec-9-en-10-ylamine

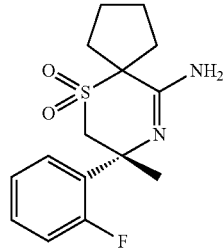 [SMILES: C[C@@]1(c2ccccc2F)CS(=O)(=O)C2(CCCC2)C(N)=N1]

To a solution of (R)-8-(5-bromo-2-fluoro-phenyl)-8-methyl-6,6-dioxo-6λ6-thia-9-aza-spiro[4.5]deca-2,9-dien-10-ylamine (245 mg, 633 µmol, Eq: 1.00) in methanol (10 ml) and ammonia (7 N in MeOH) (271 µl, 1.9 mmol, Eq: 3.0) was added at 23° C. under inert atmosphere Pd/C 10% (67.3 mg, 63.3 µmol, Eq: 0.1). The suspension was set under hydrogen (balloon) and stirred at 23° C. for 2 hours. The catalyst was filtered off, washed three times with methanol and evaporated. The residue was extracted with dichloromethane and sat. NaHCO₃-sol., the organic layer was dried over Na₂SO₄, filtered and evaporated to give the pure (R)-8-(2-fluoro-phenyl)-8-methyl-6,6-dioxo-6λ6-thia-9-aza-spiro[4.5]dec-9-en-10-ylamine (175 mg, 564 µmol, 89.1% yield) as a white solid. MS (ISP): m/z=311.5 [M+H]⁺.

A22 g: (R)-7-(5-Bromo-2-fluoro-phenyl)-7-methyl-5,5-dioxo-5λ6-thia-8-aza-spiro[3.5]non-8-en-9-ylamine

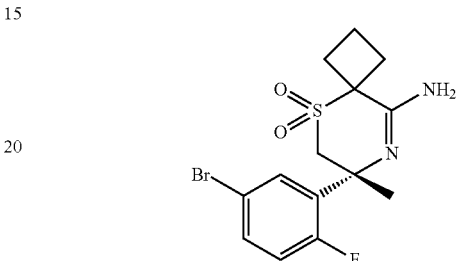

A mixture of (R)-7-(5-bromo-2-fluoro-phenyl)-7-methyl-5,5-dioxo-5λ6-thia-8-aza-spiro[3.5]nonan-9-thione (1.05 g, 2.68 mmol, Eq: 1.00) and ammonia (7 N in MeOH) (19.1 ml, 134 mmol, Eq: 50) was stirred in a sealed tube for 40 hours at 60° C. Extracted with ethyl acetate and sat. NaHCO₃-sol., dried the organic layer over Na₂SO₄, filtered and evaporated. The residue was chromatographed on 20 g silica gel with ethyl acetate to give (R)-7-(5-bromo-2-fluoro-phenyl)-7-methyl-5,5-dioxo-5λ6-thia-8-aza-spiro[3.5]non-8-en-9-ylamine (560 mg, 1.49 mmol, 55.8% yield) as a white solid. MS (ISP): m/z=375.0 [M+H]⁺ and 377.4 [M+2+H]⁺.

A22h: (R)-7-(2-Fluoro-phenyl)-7-methyl-5,5-dioxo-5λ6-thia-8-aza-spiro[3.5]non-8-en-9-ylamine

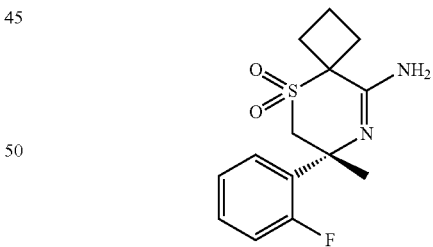

To a solution of (R)-7-(5-bromo-2-fluoro-phenyl)-7-methyl-5,5-dioxo-5λ6-thia-8-aza-spiro[3.5]non-8-en-9-ylamine (555 mg, 1.48 mmol, Eq: 1.00) in methanol (50 ml) and ammonia (7 N in MeOH) (634 µl, 4.44 mmol, Eq: 3.0) was added at 23° C. under inert atmosphere Pd/C 10% (157 mg, 148 µmol, Eq: 0.1). The suspension was set under hydrogen (balloon) and stirred at 23° C. for 2 hours. The catalyst was filtered off, washed three times with methanol/dichloromethane (1:1) and evaporated. The residue was extracted with dichloromethane and sat NaHCO₃-sol. The organic layer was dried over Na₂SO₄, filtered and evaporated to give the pure (R)-7-(2-fluoro-phenyl)-7-methyl-5,5-dioxo-5λ6- thia-8-aza-spiro[3.5]non-8-en-9-ylamine (385 mg, 1.3 mmol, 87.8% yield) as a white solid. MS (ISP): m/z=297.5 [M+H]⁺.

Synthesis of Intermediates A23

A23a: (R)-5-(2-Fluoro-5-nitro-phenyl)-5-methyl-1,1-dioxo-1,2,5,6-tetrahydro-1λ6-[1,4]thiazin-3-ylamine

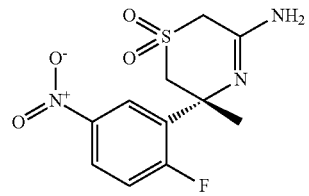 [SMILES: C[C@@]1(c2cc([N+](=O)[O-])ccc2F)CS(=O)(=O)CC(N)=N1]

To a solution of (R)-5-(2-fluoro-phenyl)-5-methyl-1,1-dioxo-1,2,5,6-tetrahydro-1λ6-[1,4]thiazin-3-ylamine (497 mg, 1.94 mmol, Eq: 1.00) in conc. sulfuric acid (14.8 g, 8.06 ml, 151 mmol, Eq: 78) was added at 0° C. 100% nitric acid (189 mg, 134 µl, 3.01 mmol, Eq: 1.55) and the mixture was stirred at 0° C. for 1 hour. Poured into sat NaHCO₃-sol., extracted with ethyl acetate, the organic layer was dried over Na₂SO₄. Removal of the solvent in vacuum left the (R)-5-(2-fluoro-5-nitro-phenyl)-5-methyl-1,1-dioxo-1,2,5,6-tetrahydro-1λ6-[1,4]thiazin-3-ylamine (584 mg, 1.94 mmol, 100% yield) as a light yellow oil. MS (ISP): m/z=302.1 [M+H]⁺.

A23b: (R)-5-(2-Fluoro-5-nitro-phenyl)-2,2,5-trimethyl-1,1-dioxo-1,2,5,6-tetrahydro-1λ6-[1,4]thiazin-3-ylamine

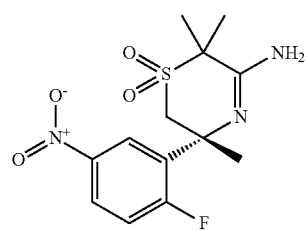 [SMILES: CC1(C)C(N)=N[C@](C)(c2cc([N+](=O)[O-])ccc2F)CS1(=O)=O]

(R)-5-(2-Fluoro-5-nitro-phenyl)-5-methyl-1,1-dioxo-1,2,5,6-tetrahydro-1λ6-[1,4]thiazin-3-ylamine (760 mg, 2.67 mmol, Eq: 1.00) was dissolved in conc. sulfuric acid (13.1 g, 7.12 ml, 134 mmol, Eq: 50), then at 0° C. fuming nitric acid (253 mg, 179 µl, 4.01 mmol, Eq: 1.5) was added dropwise. The light brown solution was stirred at 0° C. for 2 hours. The reaction mixture was poured on ice and basified with 3 N NaOH followed by extraction with dichloromethane. The organic layer was separated, dried over Na₂SO₄, filtered and evaporated to dryness to give the crude and pure (R)-5-(2-fluoro-5-nitro-phenyl)-2,2,5-trimethyl-1,1-dioxo-1,2,5,6-tetrahydro-1λ6-[1,4]thiazin-3-ylamine (950 mg, 2.74 mmol, 103% yield) as a white foam. MS (ISP): m/z=328.4 [M+H]⁺.

A23c: (R)-8-(2-Fluoro-5-nitro-phenyl)-8-methyl-6,6-dioxo-6λ6-thia-9-aza-spiro[4.5]dec-9-en-10-ylamine

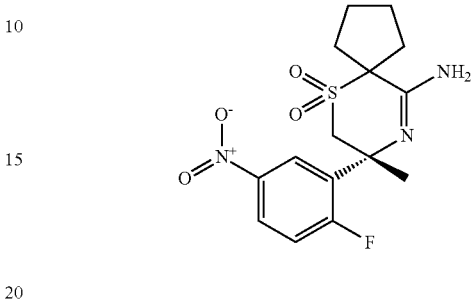

(R)-8-(2-Fluoro-phenyl)-8-methyl-6,6-dioxo-6λ6-thia-9-aza-spiro[4.5]dec-9-en-10-ylamine (172 mg, 554 µmol, Eq: 1.00) was dissolved in conc. sulfuric acid (2.72 g, 1.48 ml, 27.7 mmol, Eq: 50), then at 0° C. fuming nitric acid (52.4 mg, 37.1 µl, 831 µmol, Eq: 1.5) was added dropwise. The light brown solution was stirred at 0° C. for 2 hours. The reaction mixture was poured on ice and basified with 3 N NaOH followed by extraction with dichloromethane. The organic layer was separated, dried over Na₂SO₄, filtered and evaporated to dryness to give the crude and pure (R)-8-(2-fluoro-5-nitro-phenyl)-8-methyl-6,6-dioxo-6λ6-thia-9-aza-spiro[4.5]dec-9-en-10-ylamine (210 mg, 591 µmol, 107% yield) as an off-white foam. MS (ISP): m/z=356.5 [M+H]⁺.

A23d: (R)-7-(2-Fluoro-5-nitro-phenyl)-7-methyl-5,5-dioxo-5λ6-thia-8-aza-spiro[3.5]non-8-en-9-ylamine

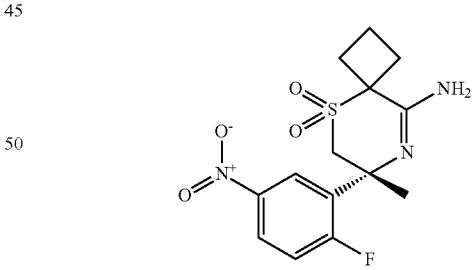

(R)-7-(2-Fluoro-phenyl)-7-methyl-5,5-dioxo-5λ6-thia-8-aza-spiro[3.5]non-8-en-9-ylamine (385 mg, 1.3 mmol, Eq: 1.00) was dissolved in conc. sulfuric acid (6.37 g, 3.46 ml, 65.0 mmol, Eq: 50). At 0° C., fuming nitric acid (123 mg, 87.1 µl, 1.95 mmol, Eq: 1.5) was added dropwise. The light brown solution was stirred at 0° C. for 2 hours. The reaction mixture was poured on ice and basified with 3 N NaOH followed by extraction with dichloromethane. The organic layer was separated, dried over Na₂SO₄, filtered and evaporated to dryness to give the crude and pure (R)-7-(2-fluoro-5-nitro-phenyl)-7-methyl-5,5-dioxo-5λ6-thia-8-aza-spiro[3.5]non-8-en-9- ylamine (470 mg, 1.38 mmol, 106% yield) as a light brown foam. MS (ISP): m/z=342.1 [M+H]⁺.

Synthesis of Intermediates A24

A24a: (R)-5-(5-Amino-2-fluoro-phenyl)-5-methyl-1,1-dioxo-1,2,5,6-tetrahydro-1λ6-[1,4]thiazin-3-ylamine

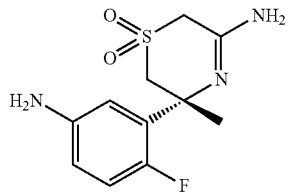 [SMILES: C[C@@]1(c2cc(N)ccc2F)CS(=O)(=O)CC(N)=N1]

A solution of (R)-5-(2-fluoro-5-nitro-phenyl)-5-methyl-1,1-dioxo-1,2,5,6-tetrahydro-1λ6-[1,4]thiazin-3-ylamine (584 mg, 1.94 mmol, Eq: 1.00) in ethanol (45 ml), triethylamine (196 mg, 270 µl, 1.94 mmol, Eq: 1.00) and Pd/C (206 mg, 194 µmol, Eq: 0.1) was hydrogenated at room temperature for 1 hour. Filtered off the catalyst, washed with ethanol, evaporated the filtrate and dried in HV to give the (R)-5-(5-amino-2-fluoro-phenyl)-5-methyl-1,1-dioxo-1,2,5,6-tetrahydro-1λ6-[1,4]thiazin-3-ylamine (460 mg, 1.7 mmol, 87.5% yield) as a an off-white foam. MS (ISP): m/z=272.4 [M+H]⁺.

A24b: (R)-5-(5-Amino-2-fluoro-phenyl)-5-methyl-1,1-dioxo-1,2,5,6-tetrahydro-1λ6-[1,4]thiazin-3-ylamine

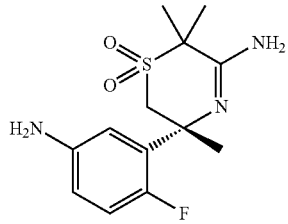 [SMILES: CC1(C)C(N)=N[C@](C)(c2cc(N)ccc2F)CS1(=O)=O]

To a solution of (R)-5-(2-fluoro-5-nitro-phenyl)-2,2,5-trimethyl-1,1-dioxo-1,2,5,6-tetrahydro-1λ6-[1,4]thiazin-3-ylamine (950 mg, 2.88 mmol, Eq: 1.00) in ethanol (50 ml) was added at 23° C. under inert atmosphere triethylamine (292 mg, 402 µl, 2.88 mmol, Eq: 1.00) and after inertisation Pd/C 10% (307 mg, 288 µmol, Eq: 0.1). The suspension was set under hydrogen (balloon) and stirred at 23° C. for 1 hour. The catalyst was filtered off, washed three times with ethanol and a mixture of dichloromethane and methanol and evaporated the combined filtrate to give the crude and nearly pure (R)-5-(5-amino-2-fluoro-phenyl)-2,2,5-trimethyl-1,1-dioxo-1,2,5,6-tetrahydro-1λ6-[1,4]thiazin-3-ylamine (760 mg, 2.54 mmol, 88.0% yield) as an off-white solid. MS (ISP): m/z=300.3 [M+H]⁺.

A24c: (R)-8-(5-Amino-2-fluoro-phenyl)-8-methyl-6,6-dioxo-6λ6-thia-9-aza-spiro[4.5]dec-9-en-10-ylamine

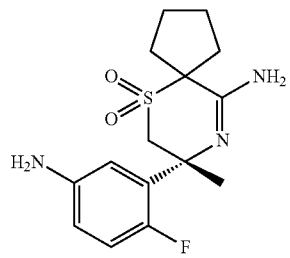 [SMILES: C[C@@]1(c2cc(N)ccc2F)CS(=O)(=O)C2(CCCC2)C(N)=N1]

To a solution of (R)-8-(2-fluoro-5-nitro-phenyl)-8-methyl-6,6-dioxo-6λ6-thia-9-aza-spiro[4.5]dec-9-en-10-ylamine (210 mg, 591 µmol, Eq: 1.00) in ethanol (10 ml) was added at 23° C. under inert atmosphere triethylamine (59.8 mg, 82.4 µl, 591 µmol, Eq: 1.00) and after inertisation Pd/C 10% (62.9 mg, 59.1 µmol, Eq: 0.1). The suspension was set under hydrogen (balloon) and stirred at 23° C. for 1 hour. The catalyst was filtered off, washed three times with ethanol and evaporated to give the crude and nearly pure (R)-8-(5-amino-2-fluoro-phenyl)-8-methyl-6,6-dioxo-6λ6-thia-9-aza-spiro[4.5]dec-9-en-10-ylamine (182 mg, 559 µmol, 94.7% yield) as an off-white foam. MS (ISP): m/z=326.5 [M+H]⁺.

A24d: (R)-7-(5-Amino-2-fluoro-phenyl)-7-methyl-5,5-dioxo-5λ6-thia-8-aza-spiro[3.5]non-8-en-9-ylamine

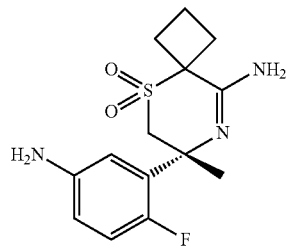 [SMILES: C[C@@]1(c2cc(N)ccc2F)CS(=O)(=O)C2(CCC2)C(N)=N1]

To a solution of (R)-7-(2-fluoro-5-nitro-phenyl)-7-methyl-5,5-dioxo-5λ6-thia-8-aza-spiro[3.5]non-8-en-9-ylamine (470 mg, 1.38 mmol, Eq: 1.00) in ethanol (10 ml) was added at 23° C. under inert atmosphere triethylamine (139 mg, 192 µl, 1.38 mmol, Eq: 1.00) and after inertisation Pd/C 10% (62.9 mg, 59.1 µmol, Eq: 0.1). The suspension was set under hydrogen (balloon) and stirred at 23° C. for 1 hour. The catalyst was filtered off, washed three times with ethanol and evaporated to give the crude (R)-7-(5-amino-2-fluoro-phenyl)-7-methyl-5,5-dioxo-5λ6-thia-8-aza-spiro[3.5]non-8- en-9-ylamine (345 mg, 1.11 mmol, 80.5% yield) as a light brown solid. MS (ISP): m/z=312.5 [M+H]+.

Synthesis of Intermediates A25

A25a: (R)—N-(bis(4-methoxyphenyl)(phenyl)methyl)-5-(5-bromo-2-fluorophenyl)-5-methyl-5,6-dihydro-2H-1,4-thiazin-3-amine

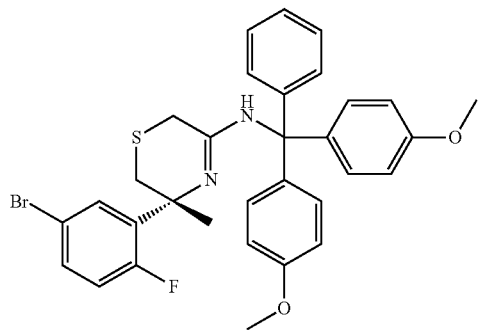 [SMILES: COc1ccc(C(NC2=N[C@](C)(c3cc(Br)ccc3F)CSC2)(c2ccccc2)c2ccc(OC)cc2)cc1]

To a solution (R)-5-(5-bromo-2-fluorophenyl)-5-methyl-5,6-dihydro-2H-1,4-thiazin-3-amine (910 mg, 3 mmol, Eq: 1.00) and triethylamine (607 mg, 836 µl, 6.00 mmol, Eq: 2) in dichloromethane (30.0 ml) at 23° C. was added 4,4'-dimethoxytrityl chloride (1.12 g, 3.3 mmol, Eq: 1.1) and the mixture was stirred at 23° C. for 2 h. The solution was concentrated in vacuum and directly subjected to silica gel flash chromatography with n-heptane and ethyl acetate to give the (R)—N-(bis(4-methoxyphenyl)(phenyl)methyl)-5-(5-bromo-2-fluorophenyl)-5-methyl-5,6-dihydro-2H-1,4-thiazin-3-amine (1.67 g, 2.76 mmol, 91.9% yield) as an off-white foam. MS (ISP): m/z=605.1 [M+H]+ and 607.2 [M+2+H]+.

Synthesis of Intermediates A26

A26a: (R)—N-(bis(4-methoxyphenyl)(phenyl)methyl)-5-(5-(diphenylmethyleneamino)-2-fluorophenyl)-5-methyl-5,6-dihydro-2H-1,4-thiazin-3-amine

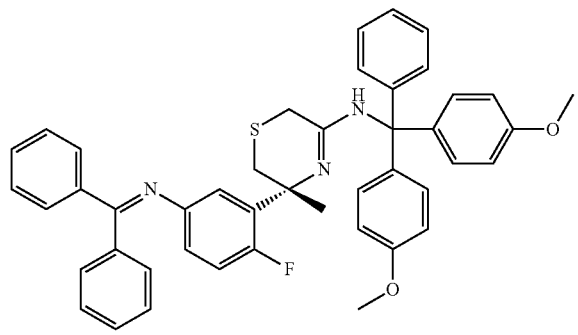 [SMILES: COc1ccc(C(NC2=N[C@](C)(c3cc(N=C(c4ccccc4)c4ccccc4)ccc3F)CSC2)(c2ccccc2)c2ccc(OC)cc2)cc1]

To a mixture of (R)—N-(bis(4-methoxyphenyl)(phenyl)methyl)-5-(5-bromo-2-fluorophenyl)-5-methyl-5,6-dihydro-2H-1,4-thiazin-3-amine (1.67 g, 2.76 mmol, Eq: 1.00), sodium tert-butoxide (795 mg, 8.27 mmol, Eq: 3), tris(dibenzylideneacetone)dipalladium(0) chloroform adduct (85.6 mg, 82.7 µmol, Eq: 0.03) and 2-di-tert-butylphosphino-2',4',6'-triisopropylbiphenyl (117 mg, 276 µmol, Eq: 0.1) in toluene (22.0 ml) at 23° C. was added benzophenone imine (1.00 g, 926 µl, 5.52 mmol, Eq: 2) this reaction mixture was stirred under argon atmosphere at 105° C. for 5 hours. Extracted with water and ethyl acetate, dried the organic layer over Na2SO4, filtered off and evaporated totally. The crude material was purified by silica gel flash chromatography with n-heptane and ethyl acetate to give the (R)—N-(bis(4-methoxyphenyl)(phenyl)methyl)-5-(5-(diphenylmethyleneamino)-2-fluorophenyl)-5-methyl-5,6-dihydro-2H-1,4-thiazin-3-amine (1.59 g, 2.25 mmol, 81.7% yield) as a yellow oil. MS (ISP): m/z=706.3 [M+H]+.

Synthesis of Intermediates A27

A27a: (R)-5-(5-amino-2-fluorophenyl)-5-methyl-5,6-dihydro-2H-1,4-thiazin-3-amine

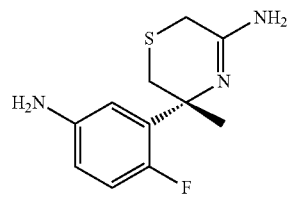 [SMILES: C[C@@]1(c2cc(N)ccc2F)CSCC(N)=N1]

To a solution of (R)—N-(bis(4-methoxyphenyl)(phenyl)methyl)-5-(5-(diphenylmethyleneamino)-2-fluorophenyl)-5-methyl-5,6-dihydro-2H-1,4-thiazin-3-amine (1.59 g, 2.25 mmol, Eq: 1.00) in dichloromethane (80 ml) at 23° C. was dropwise added TFA (12.8 g, 8.68 ml, 113 mmol, Eq: 50) and the resulting red solution was stirred at 23° C. for 3 hours, then dioxane (80 ml) was added followed by 1 M hydrochloric acid (2.25 ml, 2.25 mmol, Eq: 1.00) and stirring was continued at 23° C. for 2 hours. Poured into 25% ammonium hydroxide solution and extracted twice with dichloromethane, the combined organic layer was dried over Na2SO4, filtered off and evaporated totally. The crude material was purified by silica gel column chromatography first with ethyl acetate to remove all non-polar byproducts, then with 7 M ammonia in methanol to obtain the (R)-5-(5-amino-2-fluorophenyl)-5-methyl-5,6-dihydro-2H-1,4-thiazin-3-amine (150 mg, 627 µmol, 27.8% yield) as a light brown solid. MS (ISP): m/z=240.1 [M+H]+.

Synthesis of Intermediates A31

A31a: (R,E)-N-(1-(5-bromo-2-fluorophenyl)ethylidene)-2-methylpropane-2-sulfinamide

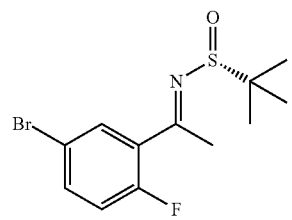 [SMILES: C/C(=N\[S@](=O)C(C)(C)C)c1cc(Br)ccc1F]

Commercially available 1-(5-bromo-2-fluorophenyl)ethanone (140 g, 645 mmol, Eq: 1.0) [CAS No. 477-89-3], (R)-2-methylpropane-2-sulfinamide (78.2, 645 mmol, Eq: 1.0) and titanium(IV) ethoxide (221 g, 204 ml, 968 mmol, Eq: 1.5)

were dissolved in tetrahydrofuran (1.19 l) and the mixture heated to 75° C. and stirred at this temperature overnight. The mixture was cooled to 50° C., sat. potassium sodium tartrate solution (1.17 l, 2.58 mol, Eq: 4) was added and the mixture stirred at this temperature for 1.5 hours. The mixture was diluted with TBME, the layers separated, the organic layer washed with sulfuric acid (0.05 M, 2.36 l, 118 mmol, Eq: 0.183), sat. $Na_2CO_3$-solution (645 ml, 645 mmol, Eq: 1.00) and brine, dried over $Na_2SO_4$ and the solvent evaporated leaving an dark orange solid, which was purified by trituration with n-heptane to give the first batch (144.7 g) as an off-white solid. From the mother liquor another batch (23.0 g) was obtained by trituration with pentane, yet another batch was obtained by silica gel column chromatography with n-heptane/ethyl acetate. Total yield of (R,E)-N-(1-(5-bromo-2-fluorophenyl)ethylidene)-2-methylpropane-2-sulfinamide (180.7 g, 564 mmol, 87.5% yield) as an off-white solid. MS (ISP): m/z=320.3 $[M+H]^+$ and 322.0 $[M+2+H]^+$.

Synthesis of Intermediates A32

A32a: (R)—N—(R)-1-(5-bromo-2-fluorophenyl)-1-cyanoethyl)-2-methylpropane-2-sulfinamide

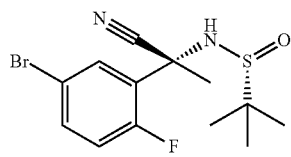 [SMILES: CC(C)(C)[S@@](=O)N[C@@](C)(C#N)c1cc(Br)ccc1F]

To a solution of diethylaluminum cyanide (1 M in toluene, 45.25 ml, 45.25 mmol) was added at 23° C. isopropanol (2.314 ml, 30.17 mmol) and the mixture was stirred at 23° C. for 30 min. The obtained solution was added dropwise within 15 min to a solution of (R,E)-N-(1-(5-bromo-2-fluorophenyl)ethylidene)-2-methylpropane-2-sulfinamide (9.66 g, 30.17 mmol) in tetrahydrofuran (452 ml) at 78° C., stirring was continued for 5 min, then slowly warmed up to −10° C. and stirred at −10° C. for 5.5 h. Poured into sat. $NaHCO_3$-sol., filtered the precipitate off, washed with ethyl acetate, washed the organic layer with brine and dried over $Na_2SO_4$. Removal of the solvent in vacuum left a yellow oil (11.38 g, d.r. 9.9:1) which was purified by crystallization from 2-methyltetrahydrofuran and n-heptane to give the first batch (4.80 g) and the second batch was obtained from the mother liquor by silica gel column chromatography with dichloromethane/TBME 95:5 (2.24 g). Total yield of (R)—N—((R)-1-(5-bromo-2-fluorophenyl)-1-cyanoethyl)-2-methylpropane-2-sulfinamide (7.04 g, 67%) as an off-white solid. MS (ISP): m/z=347.1 $[M+H]^+$ and 349.0 $[M+2+H]^+$.

Example 1

(R)—N-(3-(5-amino-3-methyl-3,6-dihydro-2H-1,4-thiazin-3-yl)-4-fluorophenyl)-5-cyanopicolinamide To a solution of 5-cyanopyridine-2-carboxylic acid (28.8 mg, 194 μmol, Eq: 1.00) in methanol (5 ml) was added at 0° C. 4-(4,6-dimethoxy-1,3,5-triazin-2-yl)-4-methylmorpholinium chloride hydrate (64.5 mg, 233 μmol, Eq: 1.2). The colorless solution was stirred at 0° C. for 30 minutes then a solution of (R)-5-(5-amino-2-fluorophenyl)-5-methyl-5,6-dihydro-2H-1,4-thiazin-3-amine (50 mg, 194 μmol, Eq: 1.00) in methanol (5 ml) was added dropwise via syringe. The reaction mixture was stirred at 23° C. for 18 h. Extracted with sat. $NaHCO_3$-sol. and ethyl acetate, dried the organic layer over $Na_2SO_4$, filtered off and evaporated totally. The crude material was purified by silica gel column chromatography with ethyl acetate and methanol, then ethyl acetate/methanol/ ammonium hydroxide to give the (R)—N-(3-(5-amino-3-methyl-3,6-dihydro-2H-1,4-thiazin-3-yl)-4-fluorophenyl)-5-cyanopicolinamide (64 mg, 173.3 μmol, 89.1% yield) as a light yellow solid. MS (ISP): m/z=370.0 $[(M+H)^+]$.

Example 2

5-Cyano-pyridine-2-carboxylic acid [3-((R)-5-amino-3-methyl-1,1-dioxo-1,2,3,6-tetrahydro-1λ6-[1,4]thiazin-3-yl)-4-fluoro-phenyl]-amide Method a): To a solution of (R)—N-(3-(5-amino-3-methyl-3,6-dihydro-2H-1,4-thiazin-3-yl)-4-fluorophenyl)-5-cyanopicolinamide (10 mg, 27.1 μmol, Eq: 1.00) in dichloromethane (2 ml) at 0° C. was added m-CPBA (80.1 mg, 325 μmol, Eq: 4) and the reaction mixture was stirred at room temperature for 2 hours. All volatiles were removed in vacuum and the residue was purified by preparative HPLC to give the 5-cyano-pyridine-2-carboxylic acid [3-((R)-5-amino-3-methyl-1,1-dioxo-1,2,3,6-tetrahydro-1λ6-[1,4]thiazin-3-yl)-4-fluoro-phenyl]-amide (3 mg, 28%, ca. 50% purity) as a white solid. MS (ISP): m/z=402.0 $[(M+H)^+]$.

Method b): To a solution of 5-cyanopicolinic acid (69.1 mg, 466 μmol, Eq: 1.1) in Methanol (6 ml) at 0° C. was added 4-(4,6-dimethoxy-1,3,5-triazin-2-yl)-4-methylmorpholinium chloride hydrate (187 mg, 636 μmol, Eq: 1.5) and the mixture was stirred at 0° C. for 15 minutes. Added (R)-5-(5-amino-2-fluoro-phenyl)-5-methyl-1,1-dioxo-1,2,5,6-tetrahydro-1λ6-[1,4]thiazin-3-ylamine (115 mg, 424 μmol, Eq: 1.00) in Methanol (6 ml) and stirred at 23° C. overnight. Poured into sat $NaHCO_3$-sol., extracted with ethyl acetate, the organic layer was dried over $Na_2SO_4$. Removal of the solvent in vacuum left a brown oil. The crude material was purified by silica gel flash chromatography (10 g): washed first with ethyl acetate, then added 5% of a 7 M solution of ammonia in methanol to give the 5-cyano-pyridine-2-carboxylic acid [3-((R)-5-amino-3-methyl-1,1-dioxo-1,2,3,6-tetrahydro-1λ6-[1,4]thiazin-3-yl)-4-fluoro-phenyl]-amide (63 mg, 157 μmol, 37.0% yield) as a light yellow solid. MS (ISP): m/z=402.4 $[(M+H)^+]$.

Example 3

5-Chloro-pyridine-2-carboxylic acid [3-((R)-5-amino-3-methyl-1,1-dioxo-1,2,3,6-tetrahydro-1λ6-[1,4]thiazin-3-yl)-4-fluoro-phenyl]-amide Prepared from 5-chloropicolinic acid (73.5 mg, 466 μmol, Eq: 1.1) and (R)-5-(5-amino-2-fluoro-phenyl)-5-methyl-1,1-dioxo-1,2,5,6-tetrahydro-1λ6-[1,4]thiazin-3-ylamine (115 mg, 424 μmol, Eq: 1.00) as described for example 2 (method b) to give the title compound (80 mg, 195 μmol, 45.9% yield) as a light yellow solid. MS (ISP): m/z=411.4 $[(M+H)^+]$ and 413.2 $[(M+2+H)^+]$.

Example 4

5-Difluoromethoxy-pyridine-2-carboxylic acid [3-((R)-5-amino-3-methyl-1,1-dioxo-1,2,3,6-tetrahydro-1λ6-[1,4]thiazin-3-yl)-4-fluoro-phenyl]-amide Prepared from 5-(difluoromethoxy)picolinic acid (69.7 mg, 369 μmol, Eq: 1.00) and (R)-5-(5-amino-2-fluoro-phenyl)-5-methyl-1,1-dioxo-1,2,5,6-tetrahydro-1λ6-[1,4]thi-azin-3-ylamine (100 mg, 369 µmol, Eq: 1.00) as described for example 2 (method b) to give the title compound (85 mg, 192 µmol, 52.1% yield) as a white foam. MS (ISP): m/z=443.4 [(M+H)].

Example 5

5-Chloro-pyridine-2-carboxylic acid [3-((R)-5-amino-3,6,6-trimethyl-1,1-dioxo-1,2,3,6-tetrahydro-1λ6-[1,4]thiazin-3-yl)-4-fluoro-phenyl]-amide Prepared from 5-chloropicolinic acid (60.8 mg, 386 µmol, Eq: 1.1) and (R)-5-(5-amino-2-fluoro-phenyl)-2,2,5-trimethyl-1,1-dioxo-1,2,5,6-tetrahydro-1λ6-[1,4]thiazin-3-ylamine (105 mg, 351 µmol, Eq: 1.00) as described for example 2 (method b) to give the title compound (150 mg, 342 µmol, 97.4% yield) as a white foam. MS (ISP): m/z=439.3 [(M+H)$^+$] and 441.2 [(M+2+H)$^+$].

Example 6

5-Cyano-pyridine-2-carboxylic acid [3-((R)-5-amino-3,6,6-trimethyl-1,1-dioxo-1,2,3,6-tetrahydro-1λ6-[1,4]thiazin-3-yl)-4-fluoro-phenyl]-amide Prepared from 5-cyanopicolinic acid (57.1 mg, 386 µmol, Eq: 1.1) and (R)-5-(5-amino-2-fluoro-phenyl)-2,2,5-trimethyl-1,1-dioxo-1,2,5,6-tetrahydro-1λ6-[1,4]thiazin-3-ylamine (105 mg, 351 µmol, Eq: 1.00) as described for example 2 (method b) to give the title compound (101 mg, 235 µmol, 67.1% yield) as a white foam. MS (ISP): m/z=430.3 [(M+H)$^+$].

Example 7

5-Methoxy-pyrazine-2-carboxylic acid [3-((R)-5-amino-3,6,6-trimethyl-1,1-dioxo-1,2,3,6-tetrahydro-1λ6-[1,4]thiazin-3-yl)-4-fluoro-phenyl]-amide Prepared from commercially available 5-methoxypyrazine-2-carboxylic acid (CAS-no. 40155-42-8) (43.2 mg, 281 µmol, Eq: 1.2) and (R)-5-(5-amino-2-fluoro-phenyl)-2,2,5-trimethyl-1,1-dioxo-1,2,5,6-tetrahydro-1λ6-[1,4]thiazin-3-ylamine (70 mg, 234 µmol, Eq: 1.00) as described for example 2 (method b) to give the title compound (67 mg, 154 µmol, 65.8% yield) as a white foam. MS (ISP): m/z=436.5 [(M+H)$^+$].

Example 8

5-Difluoromethyl-pyrazine-2-carboxylic acid [3-((R)-5-amino-3,6,6-trimethyl-1,1-dioxo-1,2,3,6-tetrahydro-1λ6-[1,4]thiazin-3-yl)-4-fluoro-phenyl]-amide Prepared from commercially available 5-(difluoromethyl)pyrazine-2-carboxylic acid (CAS-no. 1174321-06-2) (48.9 mg, 281 µmol, Eq: 1.2) and (R)-5-(5-amino-2-fluoro-phenyl)-2,2,5-trimethyl-1,1-dioxo-1,2,5,6-tetrahydro-1λ6-[1,4]thiazin-3-ylamine (70 mg, 234 µmol, Eq: 1.00) as described for example 2 (method b) to give the title compound (51 mg, 112 µmol, 47.9% yield) as a light yellow foam. MS (ISP): m/z=456.5 [(M+H)$^+$].

Example 9

5-Cyano-pyridine-2-carboxylic acid [3-((R)-10-amino-8-methyl-6,6-dioxo-6λ6-thia-9-aza-spiro[4.5]dec-9-en-8-yl)-4-fluoro-phenyl]-amide Prepared from 5-cyanopicolinic acid (27.3 mg, 184 µmol, Eq: 1.2) and (R)-8-(5-amino-2-fluoro-phenyl)-8-methyl-6,6-dioxo-6λ6-thia-9-aza-spiro[4.5]dec-9-en-10-ylamine (50 mg, 154 µmol, Eq: 1.00) as described for example 2 (method b) to give the title compound (32 mg, 70.3 µmol, 45.7% yield) as a white foam. MS (ISP): m/z=456.5 [(M+H)$^+$].

Example 10

5-Chloro-pyridine-2-carboxylic acid [3-((R)-9-amino-7-methyl-5,5-dioxo-5λ6-thia-8-aza-spiro[3.5]non-8-en-7-yl)-4-fluoro-phenyl]-amide Prepared from 5-chloropicolinic acid (48.6 mg, 308 µmol, Eq: 1.2) and (R)-7-(5-amino-2-fluoro-phenyl)-7-methyl-5,5-dioxo-5λ6-thia-8-aza-spiro[3.5]non-8-en-9-ylamine (80 mg, 257 mmol, Eq: 1.00) as described for example 2 (method b) to give the title compound (70 mg, 155 mmol, 60.4% yield) as a light yellow foam. MS (ISP): m/z=451.4 [(M+H)$^+$] and 453.2 [(M+2+H)$^+$].

Example 11

5-Cyano-pyridine-2-carboxylic acid [3-((R)-9-amino-7-methyl-5,5-dioxo-5λ6-thia-8-aza-spiro[3.5]non-8-en-7-yl)-4-fluoro-phenyl]-amide Prepared from 5-cyanopicolinic acid (33.1 mg, 224 µmol, Eq: 1.2) and (R)-7-(5-amino-2-fluoro-phenyl)-7-methyl-5,5-dioxo-5λ6-thia-8-aza-spiro[3.5]non-8-en-9-ylamine (58 mg, 186 mmol, Eq: 1.00) as described for example 2 (method b) to give the title compound (39 mg, 88.3 mmol, 47.4% yield) as a light yellow foam. MS (ISP): m/z=442.4 [(M+H)$^+$].

The invention claimed is:
1. A compound of formula I:

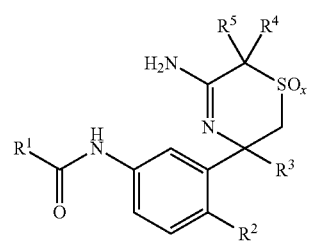

wherein:
$R^1$ is selected from the group consisting of
  i) aryl,
  ii) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
  iii) heteroaryl, and
  iv) heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$- alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;

$R^2$ is selected from the group consisting of
i) hydrogen,
ii) $C_{1-6}$-alkyl, and
iii) halogen;

$R^3$ is selected from the group consisting of
i) $C_{1-6}$-alkyl, and
ii) halogen-$C_{1-6}$-alkyl;

$R^4$ is selected from the group consisting of halogen-$C_{1-6}$-alkyl and hydrogen;

$R^5$ is selected from the group consisting of halogen-$C_{1-6}$-alkyl and hydrogen; and x is 0 or 2, or pharmaceutically acceptable salts thereof.

2. The compound according to claim 1, wherein $R^2$ is halogen.

3. The compound according to claim 1, wherein $R^2$ is F.

4. The compound according to claim 1, wherein $R^3$ is $C_{1-6}$-alkyl.

5. The compound according to claim 1, wherein $R^3$ is methyl.

6. The compound according to claim 1, wherein $R^4$ is hydrogen.

7. The compound according to claim 1, wherein $R^5$ is hydrogen.

8. The compound according to claim 1, wherein $R^1$ is heteroaryl substituted by one substituent individually selected from cyano, halogen, halogen-$C_{1-6}$-alkyl, halogen-$C_{1-6}$-alkoxy and $C_{1-6}$-alkoxy.

9. The compound according to claim 1, wherein $R^1$ is 5-cyano-pyridine-2-yl, 5-chloro-pyridine-2-yl, 5-difluoromethoxy-pyridine-2-yl, 5-methoxy-pyrazine-2-yl or 5-difluoromethyl-pyrazine-2-yl.

10. The compound according to claim 1, wherein x is 2.

11. The compound according to claim 1, selected from the group consisting of:

5-Cyano-pyridine-2-carboxylic acid [3-((R)-5-amino-3-methyl-3,6-dihydro-2H-[1,4]thiazin-3-yl)-4-fluoro-phenyl]-amide, 5-Difluoromethoxy-pyridine-2-carboxylic acid [3-((R)-5-amino-3-methyl-1,1-dioxo-1,2,3,6-tetrahydro-1$\lambda^6$-[1,4]thiazin-3-yl)-4-fluoro-phenyl]-amide, 5-Cyano-pyridine-2-carboxylic acid [3-((R)-5-amino-3-methyl-1,1-dioxo-1,2,3,6-tetrahydro-1$\lambda^6$-[1,4]thiazin-3-yl)-4-fluoro-phenyl]-amide, and 5-Chloro-pyridine-2-carboxylic acid [3-((R)-5-amino-3-methyl-1,1-dioxo-1,2,3,6-tetrahydro-1$\lambda^6$-[1,4]thiazin-3-yl)-4-fluoro-phenyl]-amide, or a pharmaceutical acceptable salt thereof.

12. A process for preparing a compound of formula I according to claim 1, comprising the step of reacting a compound of formula XI with a compound of formula XII:

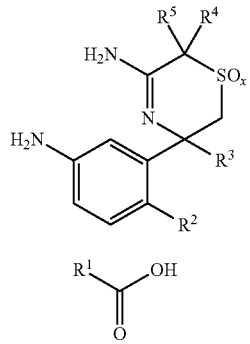

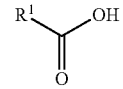

to obtain a compound of formula I, wherein x, $R^1$, $R^2$, $R^3$, $R^4$ and $R^5$ are as defined in claim 1.

13. A pharmaceutical composition, comprising a therapeutically effective amount of a compound according to claim 1 and a pharmaceutically acceptable carrier and/or a pharmaceutically acceptable auxiliary substance.

14. A method for treating Alzheimer's disease, comprising the step of administering a therapeutically effective amount of a compound according to claim 1 a human being or animal in need thereof.

* * * * *